(12) United States Patent
Poyart et al.

(10) Patent No.: US 9,551,039 B2
(45) Date of Patent: Jan. 24, 2017

(54) **RAPID DETECTION OF THE "HIGH VIRULENT" ST-17 CLONE OF GROUP B *STREPTOCOCCUS***

(71) Applicants: INSTITUT PASTEUR, Paris (FR); CENTRE NATIONAL DE LA RECHERCHE SCIENTIFIQUE, Paris (FR); UNIVERSITE PARIS DESCARTES, Paris (FR); ASSISTANCE PUBLIQUE—HOPITAUX DE PARIS, Paris (FR)

(72) Inventors: Claire Poyart, Fontenay aux Roses (FR); Marie-Cecile Lamy, Marseilles (FR); Shaynoor Dramsi, Chetenay Malabry (FR); Elisabeth Sauvage, Rambouillet (FR); Philippe Glaser, Paris (FR); Patrick Trieu-Cuot, Fontenay aux Roses (FR)

(73) Assignees: INSTITUT PASTEUR, Paris (FR); CENTRE NATIONAL DE LA RECHERCHE SCIENTIFIQUE, Paris (FR); UNIVERSITE PARIS DESCARTES, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 191 days.

(21) Appl. No.: 14/254,051

(22) Filed: Apr. 16, 2014

(65) Prior Publication Data

US 2014/0302498 A1 Oct. 9, 2014

Related U.S. Application Data

(62) Division of application No. 12/158,221, filed as application No. PCT/IB2006/004127 on Dec. 20, 2006, now Pat. No. 8,735,565.

(30) Foreign Application Priority Data

Dec. 20, 2005 (EP) .................................. 05292747

(51) Int. Cl.
*C12Q 1/68* (2006.01)

(52) U.S. Cl.
CPC ............. *C12Q 1/689* (2013.01); *C12Q 1/6883* (2013.01)

(58) Field of Classification Search
None
See application file for complete search history.

(56) References Cited

U.S. PATENT DOCUMENTS 5,629,179 A * 5/1997 Mierendorf ........ C12N 15/1096 435/91.2
6,258,539 B1 7/2001 Hunkapiller et al.
(Continued)

FOREIGN PATENT DOCUMENTS

WO 2004/099242 A2 11/2004
WO 2006069200 A2 6/2006

OTHER PUBLICATIONS

Herbert et al. BMC Microbiology. 2005. 5:31.*
(Continued)

*Primary Examiner* — Joseph G Dauner
(74) *Attorney, Agent, or Firm* — Law Office of Salvatore Arrigo and Scott Lee, LLP

(57) ABSTRACT

The present invention relates to polynucleotides enabling the rapid, simple and specific detection of Group B *Streptococcus* highly-virulent ST-17 clones.
The present invention also relates to the polypeptides encoded by said polynucleotides, as well as to antibodies directed or raised against said polypeptides.

(Continued)

The present invention also relates to kits and methods for the specific detection of Group B *Streptococcus* highly-virulent ST-17 clones, using the polynucleotides, the polypeptides or the antibodies according to the invention.

26 Claims, 9 Drawing Sheets

(56) References Cited

U.S. PATENT DOCUMENTS

| | | | |
|---|---|---|---|
| 6,432,360 B1* | 8/2002 | Church | B01J 19/0046 422/50 |
| 2001/0053519 A1 | 12/2001 | Fodor et al. | |
| 2009/0104218 A1 | 4/2009 | Tettelin et al. | |
| 2009/0162847 A1 | 6/2009 | Poyart et al. | |

OTHER PUBLICATIONS

Random Priming Technique. Retrieved on Dec. 21, 2015 from the internet: http://www.bio.davidson.edu/courses/genomics/method/randompriming.html.*
Sorensen et al. Analytical Biochemistry. 2004. 324(2):312-314.*
Davies et al. CID. 2004. 39:1129-1135.*
Reglier-Poupet et al., "Prospective evaluation of a real-time PCR assay for detection of group B streptococci in vaginal swabs from pregnant women", European Journal of Clinical Microbiology & Infection Diseases, vol. 24, pp. 355-357, 2005.
Bisharat et al., "Population structure of group B *Streptococcus* from a low-incidence region for invasive neonatal disease", Microbiology, vol. 151, pp. 1875-1881, 2005.
Musser et al., "Identification of a high-virulence clone of type III *Streptococcus agalactiae* (group B *Streptococcus*) causing invasive neonatal disease", Proceedings of the National Academy of Sciences, vol. 86, pp. 4731-4735, 1989.

* cited by examiner

Fig. 1A

```
atg aat aat aac gaa aaa aaa gta aaa tac ttt tta aga aaa aca gct      48
Met Asn Asn Asn Glu Lys Lys Val Lys Tyr Phe Leu Arg Lys Thr Ala
1               5                   10                  15
tat ggt ttg gct tca atg tca gcg gcg ttt ata gta tgt agt ggt att      96
Tyr Gly Leu Ala Ser Met Ser Ala Ala Phe Ile Val Cys Ser Gly Ile
            20                  25                  30
gta aat act cct aca gtg tct gct gat agt cct gat aca tta aaa gtc     144
Val Asn Thr Pro Thr Val Ser Ala Asp Ser Pro Asp Thr Leu Lys Val
        35                  40                  45
gaa aaa tta ggc aaa ttg aaa gat gtg aaa tca gtt cat gaa ctc aca     192
Glu Lys Leu Gly Lys Leu Lys Asp Val Lys Ser Val His Glu Leu Thr
    50                  55                  60
ccc ata tca ata ccg aac gaa tta aaa ggt gct aaa gag caa gca ctt     240
Pro Ile Ser Ile Pro Asn Glu Leu Lys Gly Ala Lys Glu Gln Ala Leu
65                  70                  75                  80
tct tca ata att tca cat cct aat ata act aat tcg gaa gta gac aaa     288
Ser Ser Ile Ile Ser His Pro Asn Ile Thr Asn Ser Glu Val Asp Lys
                85                  90                  95
cta gct agt gac tat agt ttt aga att aat aca tct aat gat gtg aac     336
Leu Ala Ser Asp Tyr Ser Phe Arg Ile Asn Thr Ser Asn Asp Val Asn
            100                 105                 110
gac gtt aaa cgt cta tta aat gaa ttt tat aac gca gtt gca agg aaa     384
Asp Val Lys Arg Leu Leu Asn Glu Phe Tyr Asn Ala Val Ala Arg Lys
        115                 120                 125
cag tta gat aca aat tct gct gac tac cgt agt aaa att gat aat atc     432
Gln Leu Asp Thr Asn Ser Ala Asp Tyr Arg Ser Lys Ile Asp Asn Ile
    130                 135                 140
agt act aca ggt ctt gcg ata gct ctt gag gct aaa gaa att tat gaa     480
Ser Thr Thr Gly Leu Ala Ile Ala Leu Glu Ala Lys Glu Ile Tyr Glu
145                 150                 155                 160
gca aat aaa tct ata tta cct cat cgt tac aaa gat tct gtt gga act     528
Ala Asn Lys Ser Ile Leu Pro His Arg Tyr Lys Asp Ser Val Gly Thr
                165                 170                 175
tat gtg aac agt ttt gag gaa aga cga agt cca gga aaa ttt aat att     576
Tyr Val Asn Ser Phe Glu Glu Arg Arg Ser Pro Gly Lys Phe Asn Ile
            180                 185                 190
tgg aat ggt cag gaa gga ttt aat gca gct caa aaa ttg tta gaa gat     624
Trp Asn Gly Gln Glu Gly Phe Asn Ala Ala Gln Lys Leu Leu Glu Asp
        195                 200                 205
gtt aaa aaa tta tta ctt gag cta caa aat tta aca aaa aat aac aaa     672
Val Lys Lys Leu Leu Leu Glu Leu Gln Asn Leu Thr Lys Asn Asn Lys
    210                 215                 220
cca aat att caa gta cct aaa caa gca cct aca gaa gct gca aaa cca     720
Pro Asn Ile Gln Val Pro Lys Gln Ala Pro Thr Glu Ala Ala Lys Pro
225                 230                 235                 240
gct ttg tca cca gaa gcc ttg aca aga ttg act aca tgg tat aat caa     768
Ala Leu Ser Pro Glu Ala Leu Thr Arg Leu Thr Thr Trp Tyr Asn Gln
                245                 250                 255
```

Fig. 1B

```
gct aaa gat ctg ctt aaa gat gat caa gta aag gac aaa tac gta gat    816
Ala Lys Asp Leu Leu Lys Asp Asp Gln Val Lys Asp Lys Tyr Val Asp
            260                 265                 270
ata ctt tca gtt caa aaa gct gtt gac caa gct tat gat cat gtg gaa    864
Ile Leu Ser Val Gln Lys Ala Val Asp Gln Ala Tyr Asp His Val Glu
        275                 280                 285
gag gga aaa ttt att acc act gat caa gca aat caa tta gct aac aag    912
Glu Gly Lys Phe Ile Thr Thr Asp Gln Ala Asn Gln Leu Ala Asn Lys
    290                 295                 300
cta cgt gat gct tta caa agt tta gaa tta aaa gat aaa aaa gta gcc    960
Leu Arg Asp Ala Leu Gln Ser Leu Glu Leu Lys Asp Lys Lys Val Ala
305                 310                 315                 320
aaa cca gta gct aaa ggt aca tac gat gtt aag tat gta gac aca gaa    1008
Lys Pro Val Ala Lys Gly Thr Tyr Asp Val Lys Tyr Val Asp Thr Glu
                325                 330                 335
gga aaa gaa gta gct aag tca cgt cac ttc gaa gga gaa gaa ggc gca    1056
Gly Lys Glu Val Ala Lys Ser Arg His Phe Glu Gly Glu Glu Gly Ala
            340                 345                 350
gct ttt gtc act tca gcg aaa gaa gta gcg ggt tac aaa ctt gtt aga    1104
Ala Phe Val Thr Ser Ala Lys Glu Val Ala Gly Tyr Lys Leu Val Arg
        355                 360                 365
acg gaa ggt gct gtt tca aat gtc ttc aca gca gga gca caa gta cgt    1152
Thr Glu Gly Ala Val Ser Asn Val Phe Thr Ala Gly Ala Gln Val Arg
    370                 375                 380
aca tat gtt tac gaa aaa gtt aaa cca gaa gtt aaa cca gac gtt aag    1200
Thr Tyr Val Tyr Glu Lys Val Lys Pro Glu Val Lys Pro Asp Val Lys
385                 390                 395                 400
cca gag gcc aaa cca gag gct aag cca gaa gtt aaa cca gac gtt aag    1248
Pro Glu Ala Lys Pro Glu Ala Lys Pro Glu Val Lys Pro Asp Val Lys
                405                 410                 415
cca gag gcc aaa cca gag gct aag cca gaa gtt aaa tca gac gtt aag    1296
Pro Glu Ala Lys Pro Glu Ala Lys Pro Glu Val Lys Ser Asp Val Lys
            420                 425                 430
cca gag gct aag cca gaa gcc aaa cca gag gct aaa cca gaa gtt aaa    1344
Pro Glu Ala Lys Pro Glu Ala Lys Pro Glu Ala Lys Pro Glu Val Lys
        435                 440                 445
cca gac gtt aag cca gag gct aaa cca gaa gcc aag cca gca acc aaa    1392
Pro Asp Val Lys Pro Glu Ala Lys Pro Glu Ala Lys Pro Ala Thr Lys
    450                 455                 460
aaa tcg gtt aat act agc gga aac ttg gtg gct aaa aaa gct att gaa    1440
Lys Ser Val Asn Thr Ser Gly Asn Leu Val Ala Lys Lys Ala Ile Glu
465                 470                 475                 480
aac aaa aag tat agt aaa aaa tta cca tca acg ggt gaa gcc gca agt    1488
Asn Lys Lys Tyr Ser Lys Lys Leu Pro Ser Thr Gly Glu Ala Ala Ser
                485                 490                 495
cca ctc tta gca att gta tca cta att gtt atg tta agt gca ggt ctt    1536
Pro Leu Leu Ala Ile Val Ser Leu Ile Val Met Leu Ser Ala Gly Leu
            500                 505                 510
att acg ata gtt tta aag cat aaa aaa aat taa                        1569
Ile Thr Ile Val Leu Lys His Lys Lys Asn
        515                 520
```

```
atg aat aat aac gaa aaa aaa gta aaa tac ttt tta aga aaa aca gct    48
Met Asn Asn Asn Glu Lys Lys Val Lys Tyr Phe Leu Arg Lys Thr Ala
1               5                   10                  15
tat ggt ttg gct tca atg tca gcg gcg ttt ata gta tgt agt ggt att    96
Tyr Gly Leu Ala Ser Met Ser Ala Ala Phe Ile Val Cys Ser Gly Ile
                20                  25                  30
gta                                                                99
Val
```

B. S6

```
aaa cca aat att caa gta cct aaa caa gca cct aca gaa gct gca aaa    48
Lys Pro Asn Ile Gln Val Pro Lys Gln Ala Pro Thr Glu Ala Ala Lys
1               5                   10                  15
cca gct ttg tca cca gaa gcc ttg aca aga ttg act aca tgg tat aat    96
Pro Ala Leu Ser Pro Glu Ala Leu Thr Arg Leu Thr Thr Trp Tyr Asn
                20                  25                  30
caa gct aaa gat ctg ctt aaa gat gat caa gta aag gac aaa tac gta   144
Gln Ala Lys Asp Leu Leu Lys Asp Asp Gln Val Lys Asp Lys Tyr Val
                35                  40                  45
gat ata ctt tca gtt caa aaa gct gtt gac caa gct tat gat cat gtg   192
Asp Ile Leu Ser Val Gln Lys Ala Val Asp Gln Ala Tyr Asp His Val
        50                  55                  60
gaa gag gga aaa ttt att acc act gat caa gca aat caa tta gct aac   240
Glu Glu Gly Lys Phe Ile Thr Thr Asp Gln Ala Asn Gln Leu Ala Asn
65              70                  75                  80
aag cta cgt gat gct tta caa agt tta gaa tta aaa gat aaa aaa gta   288
Lys Leu Arg Asp Ala Leu Gln Ser Leu Glu Leu Lys Asp Lys Lys Val
                85                  90                  95
gcc                                                               291
Ala
```

C. S7

```
aag cca gag gcc aaa cca gag gct aag cca gaa gtt aaa cca gac gtt    48
Lys Pro Glu Ala Lys Pro Glu Ala Lys Pro Glu Val Lys Pro Asp Val
1               5                   10                  15
aag cca gag gcc aaa cca gag gct aag cca gaa gtt aaa tca gac gtt    96
Lys Pro Glu Ala Lys Pro Glu Ala Lys Pro Glu Val Lys Ser Asp Val
                20                  25                  30
aag cca gag gct aag cca gaa gcc aaa cca gag gct aaa cca gaa gtt   144
Lys Pro Glu Ala Lys Pro Glu Ala Lys Pro Glu Ala Lys Pro Glu Val
                35                  40                  45
aaa cca gac gtt aag cca gag gct aaa cca gaa gcc                   180
Lys Pro Asp Val Lys Pro Glu Ala Lys Pro Glu Ala
        50                  55                  60
```

| | | | | | | | | | | | | | | | | |
|---|---|---|---|---|---|---|---|---|---|---|---|---|---|---|---|---|
| aag | cca | gca | acc | aaa | aaa | tcg | gtt | aat | act | agc | gga | aac | ttg | gtg | gct | 48 |
| Lys | Pro | Ala | Thr | Lys | Lys | Ser | Val | Asn | Thr | Ser | Gly | Asn | Leu | Val | Ala | |
| 1 | | | | 5 | | | | | 10 | | | | | 15 | | |
| aaa | aaa | gct | att | gaa | aac | aaa | aag | tat | agt | aaa | aaa | tta | cca | tca | acg | 96 |
| Lys | Lys | Ala | Ile | Glu | Asn | Lys | Lys | Tyr | Ser | Lys | Lys | Leu | Pro | Ser | Thr | |
| | | | 20 | | | | | 25 | | | | | 30 | | | |
| ggt | gaa | gcc | gca | agt | cca | ctc | tta | gca | att | gta | tca | cta | att | gtt | atg | 144 |
| Gly | Glu | Ala | Ala | Ser | Pro | Leu | Leu | Ala | Ile | Val | Ser | Leu | Ile | Val | Met | |
| | | | | 35 | | | | | 40 | | | | | 45 | | |
| tta | agt | gca | ggt | ctt | att | acg | ata | gtt | tta | aag | cat | aaa | aaa | aat | taa | 192 |
| Leu | Ser | Ala | Gly | Leu | Ile | Thr | Ile | Val | Leu | Lys | His | Lys | Lys | Asn | | |
| | | 50 | | | | | 55 | | | | | 60 | | | | |

B. S10

| | | | | | | | | | | | | | | | | |
|---|---|---|---|---|---|---|---|---|---|---|---|---|---|---|---|---|
| aat | act | cct | aca | gtg | tct | gct | gat | agt | cct | gat | aca | tta | aaa | gtc | gaa | 48 |
| Asn | Thr | Pro | Thr | Val | Ser | Ala | Asp | Ser | Pro | Asp | Thr | Leu | Lys | Val | Glu | |
| 1 | | | | 5 | | | | | 10 | | | | | 15 | | |
| aaa | tta | ggc | aaa | ttg | aaa | gat | gtg | aaa | tca | gtt | cat | gaa | ctc | aca | ccc | 96 |
| Lys | Leu | Gly | Lys | Leu | Lys | Asp | Val | Lys | Ser | Val | His | Glu | Leu | Thr | Pro | |
| | | | 20 | | | | | 25 | | | | | 30 | | | |
| ata | tca | ata | ccg | aac | gaa | tta | aaa | ggt | gct | aaa | gag | caa | gca | ctt | tct | 144 |
| Ile | Ser | Ile | Pro | Asn | Glu | Leu | Lys | Gly | Ala | Lys | Glu | Gln | Ala | Leu | Ser | |
| | | | | 35 | | | | | 40 | | | | | 45 | | |
| tca | ata | att | tca | cat | cct | aat | ata | act | aat | tcg | gaa | gta | gac | aaa | cta | 192 |
| Ser | Ile | Ile | Ser | His | Pro | Asn | Ile | Thr | Asn | Ser | Glu | Val | Asp | Lys | Leu | |
| | | 50 | | | | | 55 | | | | | 60 | | | | |
| gct | agt | gac | tat | agt | ttt | aga | att | aat | aca | tct | aat | gat | gtg | aac | gac | 240 |
| Ala | Ser | Asp | Tyr | Ser | Phe | Arg | Ile | Asn | Thr | Ser | Asn | Asp | Val | Asn | Asp | |
| 65 | | | | | 70 | | | | | 75 | | | | | 80 | |
| gtt | aaa | cgt | cta | tta | aat | gaa | ttt | tat | aac | gca | gtt | gca | agg | aaa | cag | 288 |
| Val | Lys | Arg | Leu | Leu | Asn | Glu | Phe | Tyr | Asn | Ala | Val | Ala | Arg | Lys | Gln | |
| | | | | 85 | | | | | 90 | | | | | 95 | | |
| tta | gat | aca | aat | tct | gct | gac | tac | cgt | agt | aaa | att | gat | aat | atc | agt | 336 |
| Leu | Asp | Thr | Asn | Ser | Ala | Asp | Tyr | Arg | Ser | Lys | Ile | Asp | Asn | Ile | Ser | |
| | | | 100 | | | | | 105 | | | | | 110 | | | |
| act | aca | ggt | ctt | gcg | ata | gct | ctt | gag | gct | aaa | gaa | att | tat | gaa | gca | 384 |
| Thr | Thr | Gly | Leu | Ala | Ile | Ala | Leu | Glu | Ala | Lys | Glu | Ile | Tyr | Glu | Ala | |
| | | | | 115 | | | | | 120 | | | | | 125 | | |
| aat | aaa | tct | ata | tta | cct | cat | cgt | tac | aaa | gat | tct | gtt | gga | act | tat | 432 |
| Asn | Lys | Ser | Ile | Leu | Pro | His | Arg | Tyr | Lys | Asp | Ser | Val | Gly | Thr | Tyr | |
| | | 130 | | | | | 135 | | | | | 140 | | | | |
| gtg | aac | agt | ttt | gag | gaa | aga | cga | agt | cca | gga | aaa | ttt | aat | att | tgg | 480 |
| Val | Asn | Ser | Phe | Glu | Glu | Arg | Arg | Ser | Pro | Gly | Lys | Phe | Asn | Ile | Trp | |
| 145 | | | | | 150 | | | | | 155 | | | | | 160 | |
| aat | ggt | cag | gaa | gga | ttt | aat | gca | gct | caa | aaa | ttg | tta | gaa | gat | gtt | 528 |
| Asn | Gly | Gln | Glu | Gly | Phe | Asn | Ala | Ala | Gln | Lys | Leu | Leu | Glu | Asp | Val | |
| | | | | 165 | | | | | 170 | | | | | 175 | | |
| aaa | aaa | tta | tta | ctt | gag | cta | caa | aat | tta | aca | aaa | aat | aac | | | 570 |
| Lys | Lys | Leu | Leu | Leu | Glu | Leu | Gln | Asn | Leu | Thr | Lys | Asn | Asn | | | |
| | | | 180 | | | | | 185 | | | | | 190 | | | |

```
aaa cca gta gct aaa ggt aca tac gat gtt aag tat gta gac aca gaa     48
Lys Pro Val Ala Lys Gly Thr Tyr Asp Val Lys Tyr Val Asp Thr Glu
1                5                  10                 15
gga aaa gaa gta gct aag tca cgt cac ttc gaa gga gaa gaa ggc gca     96
Gly Lys Glu Val Ala Lys Ser Arg His Phe Glu Gly Glu Glu Gly Ala
                20                  25                 30
gct ttt gtc act tca gcg aaa gaa gta gcg ggt tac aaa ctt gtt aga    144
Ala Phe Val Thr Ser Ala Lys Glu Val Ala Gly Tyr Lys Leu Val Arg
            35                  40                 45
acg gaa ggc gct gtt tca aat gtc ttc aca gca gga gca caa gta cgt    192
Thr Glu Gly Ala Val Ser Asn Val Phe Thr Ala Gly Ala Gln Val Arg
        50                  55                  60
aca tat gtt tac gaa aaa gta gcc                                    216
Thr Tyr Val Tyr Glu Lys Val Ala
65                  70
```

B. S11b

```
aaa cca gta gct aaa ggt aca tac gat gtt aag tat gta gac aca gaa     48
Lys Pro Val Ala Lys Gly Thr Tyr Asp Val Lys Tyr Val Asp Thr Glu
1                5                  10                 15
gga aaa gaa gta gct aag tca cgt cac ttc gaa gga gaa gaa ggc gca     96
Gly Lys Glu Val Ala Lys Ser Arg His Phe Glu Gly Glu Glu Gly Ala
                20                  25                 30
gct ttt gtc act tca gcg aaa gaa gta gcg ggt tac aaa ctt gtt aga    144
Ala Phe Val Thr Ser Ala Lys Glu Val Ala Gly Tyr Lys Leu Val Arg
            35                  40                 45
acg gaa ggt gct gtt tca aat gtc ttc aca gca gga gca caa gta cgt    192
Thr Glu Gly Ala Val Ser Asn Val Phe Thr Ala Gly Ala Gln Val Arg
        50                  55                  60
aca tat gtt tac gaa aaa gtt aaa cca gaa gtt aaa cca gac gtt        237
Thr Tyr Val Tyr Glu Lys Val Lys Pro Glu Val Lys Pro Asp Val
65                  70                  75
```

```
atacaaattc tgctgactac cgtagtaaaa ttgataatat cagtactaca ggtcttgcga    60
tagctcttga ggctaaagaa atttatgaag caaataaatc tatattacct catcgttaca   120
aagattctgt tggaacttat gtgaacagtt ttgaggaaag acgaagtcca ggaaaattta   180
atatttggaa tggtcaggaa ggatttaa                                       208
```

B. O13/ST-17AS

```
cctcatcgtt acaaagattc tgttggaact tatgtgaaca gttttgagga agacgaagt     60
ccaggaaaat ttaatatttg gaatggtcag gaaggattta a                       101
```

C. O13/O12

```
cctcatcgtt acaaagattc tgttggaact tatgtgaaca gttttgagga agacgaagt     60
ccaggaaaat ttaatatttg gaatggtcag gaaggattta atgcagc                 107
```

D. ST-17S/O12

```
atacaaattc tgctgactac cgtagtaaaa ttgataatat cagtactaca ggtcttgcga    60
tagctcttga ggctaaagaa atttatgaag caaataaatc tatattacct catcgttaca   120
aagattctgt tggaacttat gtgaacagtt ttgaggaaag acgaagtcca ggaaaattta   180
atatttggaa tggtcaggaa ggatttaatg cagc                                214
```

E. O11/ST-17AS

```
ggcttcaatg tcagcggcgt ttatagtatg tagtggtatt gtaaatactc ctacagtgtc    60
tgctgatagt cctgatacat aaaagtcga aaaattaggc aaattgaaag atgtgaaatc   120
agttcatgaa ctcacaccca tatcaatacc gaacgaatta aaaggtgcta aagagcaagc   180
actttcttca ataatttcac atcctaatat aactaattcg gaagtagaca aactagctag   240
tgactatagt tttagaatta atacatctaa tgatgtgaac gacgttaaac gtctattaaa   300
tgaattttat aacgcagttg caaggaaaca gttagataca aattctgctg actaccgtag   360
taaaattgat aatatcagta ctacaggtct tgcgatagct cttgaggcta aagaaattta   420
tgaagcaaat aaatctatat acctcatcg ttacaaagat tctgttggaa cttatgtgaa   480
cagttttgag gaaagacgaa gtccaggaaa atttaatatt tggaatggtc aggaaggatt   540
taa                                                                  543
```

F. O11/O12

```
ggcttcaatg tcagcggcgt ttatagtatg tagtggtatt gtaaatactc ctacagtgtc    60
tgctgatagt cctgatacat aaaagtcga aaaattaggc aaattgaaag atgtgaaatc   120
agttcatgaa ctcacaccca tatcaatacc gaacgaatta aaaggtgcta aagagcaagc   180
actttcttca ataatttcac atcctaatat aactaattcg gaagtagaca aactagctag   240
tgactatagt tttagaatta atacatctaa tgatgtgaac gacgttaaac gtctattaaa   300
tgaattttat aacgcagttg caaggaaaca gttagataca aattctgctg actaccgtag   360
taaaattgat aatatcagta ctacaggtct tgcgatagct cttgaggcta aagaaattta   420
tgaagcaaat aaatctatat acctcatcg ttacaaagat tctgttggaa cttatgtgaa   480
cagttttgag gaaagacgaa gtccaggaaa atttaatatt tggaatggtc aggaaggatt   540
taatgcagc                                                            549
```

RAPID DETECTION OF THE "HIGH VIRULENT" ST-17 CLONE OF GROUP B STREPTOCOCCUS

REFERENCE TO RELATED APPLICATIONS

This application is a divisional of U.S. application Ser. No. 12/158,221, which is the U.S. National Stage of International Application PCT/IB06/04127, filed Dec. 20, 2006, which claims priority to EP Application 05292747.2, filed Dec. 20, 2005, all of which are incorporated by reference.

FIELD OF THE INVENTION

The present invention relates to polynucleotides enabling the rapid, simple and specific detection of Group B *Streptococcus* highly-virulent ST-17 clones.

The present invention also relates to the polypeptides encoded by said polynucleotides, as well as to antibodies directed or raised against said polypeptides.

The present invention also relates to kits and methods for the specific detection of Group B *Streptococcus* highly-virulent ST-17 clones, using the polynucleotides, the polypeptides or the antibodies according to the invention.

BACKGROUND/PRIOR ART

*Streptococcus agalactiae*, also known as Group B *Streptococcus* (GBS), is a capsulated Gram-positive bacterium that can be found in the gastro-intestinal and genito-urinary tracts of up to 40% of healthy adults. This commensal organism can be considered as a leading cause of neonatal morbidity and mortality in the developed countries (Schrag et al., 2002).

The most predictive factor of neonatal infection by GBS relates to the transmission of *S. agalactiae* from the mother to the neonate. This contamination generally occurs during the crossing of the genital tract, through inhalation and ingestion of contaminated amniotic liquid. It is estimated that at least 50% of newborns exposed to GBS will be colonized and that 2% will develop an infection (Schuchat, 1999). Invasive GBS infections in newborns frequently result in pneumonia and bacteraemia (approximately 80% of cases), less commonly in meningitis (10%), and death in rare instances (4%) (Schuchat, 1999). GBS-induced meningitis can lead to significant morbidity, resulting in severe neurological damage.

Approximately 80% of GBS neonatal infections occur within the first week of life and are thus designated early-onset diseases (EOD). Most of the cases of EOD are clinically apparent on the day of birth or within the first 72 hours. Late-onset diseases (LOD) usually occur in infants between 1 week and 3 months of age.

To date, nine capsular serotypes of GBS have been described: Ia, Ib, and II through VIII. Among these, serotype III GBS strains are of particular importance, as they are responsible for the majority of invasive neonatal infections and for nearly all neonatal meningitis cases in North America and Europe.

Studies also suggested that only a limited number of strains of serotype III, defined as "highly-virulent clones", can cause a large majority of neonatal invasive diseases, and almost all meningitis cases. Recently, molecular epidemiological studies demonstrated that most GBS strains responsible for invasive neonatal infections belong to a homogeneous serotype III clone designated ST-17 (Jones et al, 2003; Luan et al, 2005).

Among the strategies set up to decrease neonatal infection by GBS, the implementation of selective intrapartum antimicrobial prophylaxis, based on either screening-strategies or risk-analyses, has lowered the incidence of EOD in the United-States and other western countries, but not that of LOD (Schrag, 2004). As progress continues to be made in EOD prevention, LOD now represents a growing proportion of all GBS neonatal infections (Schrag, 2004). Moreover, the implementation of prophylactic guidelines has increased the use of antibiotics, leading to the emergence of antimicrobial resistance in both GBS and in other perinatal pathogens.

An alternative strategy would be the early identification of highly virulent GBS in order to set up a targeted antibiotic prophylaxis.

The current recommendations to prevent Group B streptococcal disease involve screening for GBS colonization in pregnant women at 34 to 38 week gestation to identify candidates for intrapartum antibioprophylaxis. However, the culture method remains the "gold standard" technique to detect the presence of GBS in vaginal secretions. Although the culture method allows an efficient identification of GBS members, it however fails to distinguish the potentially high-virulence clones from the others.

Recent epidemiological molecular methods have proven to be powerful techniques for the characterization of phylogenetic lineages among GBS isolates pertaining to the same serotype. Among these methods, multilocus sequencing typing (MLST), multilocus enzyme electrophoresis (MLEE), pulse-field gel electrophoresis (PFGE), restriction digest pattern and restriction fragment length polymorphism (RFLP) have been especially used.

However, these techniques are fastidious and time consuming and cannot be used routinely in obstetric settings to test for the presence of highly-virulent ST-17 strains during pregnancy or at the time of delivery.

Thus, the characterization of genes specific for highly virulent GBS strains would be of major clinical importance, not only to limit the use of antibiotics, but also for the follow-up of neonates colonized by such highly virulent strains.

SUMMARY OF THE INVENTION

An object of the present invention relates to the identification of a ST-17 specific allele of the gene gbs2018, thereby rendering possible the rapid and efficient detection of infection due to highly-virulent serotype III GBS strains.

In particular, the present invention relates to polynucleotides consisting of said gene or of fragments thereof.

The invention also relates to the polypeptides encoded by the polynucleotides defined herein.

The invention also relates to polyclonal and monoclonal antibodies directed against the polypeptides encoded by the polynucleotides defined herein.

The invention further encompasses methods of detection of the presence of ST-17 strains in a biological sample.

Another aspect of the invention concerns kits for detection of GBS ST-17 strains from a biological sample.

DETAILED DESCRIPTION

The present invention relates to a polynucleotide selected from the following group:
a) a group B *Streptococcus* gene encoding a surface protein Gbs2018 of a strain of the ST-17 clone, wherein said gene comprises a nucleic acid sequence having the sequence S10 (FIG. 3b) of SEQ ID NO 5, and which further comprises a domain consisting in at least one nucleic acid sequence having at least one of the sequence S11a (FIG. 4a) of SEQ ID NO 13 and/or the sequence S11b (FIG. 4b) of SEQ ID NO 15;
b) a polynucleotide hybridizing in stringent conditions with the gene of a);
c) a fragment derived from a group B *Streptococcus* gene defined in a) or a corresponding fragment derived from a polynucleotide hybridizing in stringent conditions with the gene defined in a), wherein such fragment is suitable for use in a process for the specific detection of a GBS strain of the ST-17 clone or codes for a polypeptide comprising epitopes of said surface protein Gbs2018;
d) a polynucleotide which is substantially complementary to a fragment of said gene defined in a) or of said polynucleotide defined in b), or of said fragment defined in c) and which is suitable for use in a process for the specific detection of a GBS strain of the ST-17 clone or codes for a polypeptide comprising epitopes of said surface protein Gbs2018;
e) with the proviso that the polynucleotide is not the gene having the coding sequence designated gbs2018-NEM318 (FIG. 1) of SEQ ID NO 1.

A particular polynucleotide of the invention is one which is selected from the following group:
a) a group B *Streptococcus* gene encoding a surface protein Gbs2018 of a strain of the ST-17 clone, wherein said gene comprises a nucleic acid sequence having the sequence S10 (FIG. 3b) of SEQ ID NO 5, and which further comprises a domain consisting in at least one nucleic acid sequence having at least two copies of the nucleic acid sequence S11a (FIG. 4a) of SEQ ID NO 13 or of the nucleic acid sequence S11b (FIG. 4b) of SEQ ID NO 15 or at least one copy of each nucleic acid sequences S11a and S11b;
b) a polynucleotide hybridizing in stringent conditions with the gene of a), including hybridizing with the S10 segment and the two segments either identical or different, selected among the group of S11a segment and S11b segment;
c) a fragment derived from a group B *Streptococcus* gene as defined in a) or derived from a polynucleotide hybridizing in stringent conditions with said gene, wherein such fragment is suitable for use in a process for the specific detection of a GBS strain of the ST-17 clone or codes for a polypeptide comprising epitopes of said surface protein Gbs2018;
d) a polynucleotide which is substantially complementary to a fragment of said gene defined in a) or of said polynucleotide defined in b), or of said fragment defined in c) and which is suitable for use in a process for the specific detection of a GBS strain of the ST-17 clone or codes for a polypeptide comprising epitopes of said surface protein Gbs2018.

In a particular embodiment, the defined fragments of the invention are suitable for use in a process for the detection, especially for the specific detection, of a GBS strain of the ST-17 clone.

The expression "substantially complementary" as used herein means that the considered polynucleotide is either fully complementary to the polynucleotide of reference, or that it is different from the letter at some positions (having nevertheless substantially the same length) with the proviso that it hybridizes in stringent conditions with the polynucleotide of reference.

As used therein, "polynucleotide" refers to a nucleic acid which is different from the genome of *S. agalactiae*. In a particular embodiment, such a polynucleotide is derived from the genome of *S. agalactiae* and especially is a gene or a fragment of a gene of *S. agalactiae*. In that case, the polynucleotide is isolated or purified, i.e., is separated from its natural environment in the genome. The polynucleotide of the invention said to be derived from the genome of *S. agalatiae* comprises and in particular reflects the genetic information which is contained in the sequence which is its counterpart in the genome.

The polynucleotide of the invention can accordingly have a sequence which has an exact counterpart in the genome of the *S. agalactiae* from which its derives or a substantial counterpart, meaning that its nucleotide composition can vary with respect to said sequence in the genome, to the extent that the modification in the sequence does not essentially affect the property of the obtained polynucleotide to hybridize in stringent conditions with the genomic sequence from which it derives.

Hence, a polynucleotide derived from the gbs2018 gene can bear substitution, addition or deletion of some of the nucleotide(s) of the original gene.

The polynucleotide of the invention can be prepared having recourse to any available methods, including extraction from the genome, involving for example use of restriction enzymes and/or synthesis, including chemical synthesis, and/or recombinant technology.

Any ex vivo generation method and the like, as well as combinations thereof is suitable for such preparation. In a specific embodiment, these methods may comprise extraction of the nucleic acid from its natural environment for example by hydrolyzation with restriction enzymes, followed by amplification of the polynucleotide of interest and/or synthesis, especially chemical synthesis.

The term "polynucleotide" is used interchangeably with "nucleic acid" and "oligonucleotide" and includes, but is not limited to DNA, RNA, a combination of DNA and RNA sequences of more than two nucleotides. The polynucleotide of the invention is either double stranded or single stranded.

By "gene", it is meant a nucleic acid molecule whose nucleotide sequence comprises or consists in a sequence encoding a polypeptide, i.e., comprises or consists in an ORF (Open Reading Frame). Hence, a gene according to the invention encompasses a nucleic acid molecule whose sequence does not comprise promoter sequences or regulation sequences that are usually placed upstream or downstream of the coding sequence. In such a case the gene is the molecule restricted to the coding sequence. The expression "gene" also encompasses the molecule having both the coding sequence for a polypeptide and regulatory sequences including promoter and/or terminator sequences. Said regulatory sequences can be the native sequences present in the genome of reference of *S. agalactiae* or can be heterologous sequences, i.e., sequences that are not naturally associated with the coding sequence in the genome.

In a particular embodiment, the word "gene" refers to the gbs2018 gene of a Group B *Streptococcus* of the ST-17 clone. A particular gbs2018 gene can be illustrated by the polynucleotide gbs21018-NEM318 (FIG. 1) of SEQ ID No 1.

As used herein, "the ST-17 clone" refers to bacterial strains belonging to the *Streptococcus agalactiae* strains, also known as Group B *Streptococcus* (GBS) and more particularly belonging to the "type III" GBS serotype, especially belonging to the phylogenetic lineage of high-virulent strains [Jones N et al., 2003; Luan S L et al., 2005].

Identification and characterization of the sequence type implies known methods including but not limited to, culture methods or molecular methods such as multilocus enzyme electrophoresis (MLEE), multilocus sequencing typing (MLST), pulse-field gel electophoresis (PFGE), restriction digest pattern, restriction fragment length polymorphism (RFLP) and the like, as well as combinations thereof. The inventors have carried out genetic studies on various Sequence Types of GBS strains and have achieved a phylogenic tree comprising three clusters, i.e., clusters A, B and C wherein cluster C represents and contains only strains of Sequence Type 17. ST-17 comprises, especially, the following strains CCH56, CCH63, CCH76, CCH71, CCH77, CCH60, CCH80, CCH81, CCH69, CCH73, CCH82, BM110 [Musser J M et al., 1989; Stålhammar-Carlemalm M, 1993], NEM623, COH1 [Wessels M R and al., 1989] and NEM318 [Gaillot et al., 1997].

One particular example of ST-17 strain is the *Streptococcus agalactiae* NEM318, deposited at the Collection Nationale de Cultures de Microorganismes (C.N.C.M.), INSTITUT PASTEUR, 25 rue du Docteur Roux, F-75724 PARIS CEDEX 15, under the accession number CNCM I-3537 on Dec. 2, 2005. NEM318 is a serotype III, tetracycline resistant strain of ST-17 type clone [Gaillot et al., 1997]. NEM318 is grown at 37° C. in Todd Hewitt medium, whether in liquid culture under shaking, or on agar plates.

The terms "segment S10" or "S10", as used in the present application, refer to a polynucleotide or segment that is specific of the allelic form of the gene gbs2018 of a GBS strain of the Sequence Type 17 i.e., it is not found in strains of serotype III which are not ST-17 strains. The "segment S10" or "S10" can be defined as an internal region of the gbs2018 gene following the N-terminal sequence of the gene which is shared by the GBS strains. A particular polynucleotide corresponding to the S10 segment has for example 570 nucleotides and has the nucleotide sequence S10 (FIG. 3*b*) of SEQ ID No 5, which is comprised between nucleotide positions 100 and 669 in the sequence of the ST-17 allelic form of the gbs2018 gene of sequence gbs2018-NEM318 (C.N.C.M I-3537 and FIG. 1) of SEQ ID No 1.

The terms "segment S11" or "S11", as used in the present application, refer to a polynucleotide (or segment) that is specific of the allelic form of the gene gbs2018 of a GBS strain of the Sequence Type 17 i.e., it has not been found in available strains of serotype III which are not ST-17 strains. The "segment S11" or "S11" can be defined as an internal region of the gbs2018 gene. Depending on the ST-17 strains, the ST-17 allelic form of the gene gbs2018 can either contain one or two copies of the S11 segment. By copies, it is meant two S11 sequences that are either identical or different but homologous. Particular homologous polynucleotides for the S11 segment are for example the sequence S11a (FIG. 4*a*) of SEQ ID NO 13 and the sequence S11b (FIG. 4*b*) of SEQ ID NO 15.

In an embodiment, the invention relates to polynucleotides which are gbs2018 genes of a strain of the ST-17 clone comprising one copy of the sequence S11a (FIG. 4*a*) of SEQ ID NO 13 and one copy of the sequence S11b (FIG. 4*b*) of SEQ ID NO 15. Especially, the gbs2018 gene of the invention comprises a domain with contiguous S11a and S11b segments.

The invention also relates to polynucleotides which are gbs2018 genes of a strain of the ST-17 clone comprising two copies of the S11a segment or two copies of the S11b segment, either contiguous or not in the gene.

The invention also concerns the use of polynucleotides which are gbs2018 genes of a strain of the ST-17 clone, wherein only one copy of the S11 segment is present.

But in a particular embodiment, the invention does not encompass the particular gene having sequence disclosed for the COH-1 strain in Tettelin H et al, 2005, corresponding to the sequence gbs2018-NEM318 of SEQ ID NO 1. The invention nevertheless comprises the fragments of said gene as defined in the present application, and the use of the gene and the fragments thereof, as defined in the present application.

It has been shown by the inventors that the S10 and S11 segments in gbs2018 genes are determinant in the classification of a GBS strain as an ST-17 strain (confer FIG. 6). It has also been shown by the inventors that the presence of S10 and/or one or more, especially 2, copies of the S11 segment (either S11a or S11b or combinations thereof as disclosed herewith) allows the discrimination among two sublineages of ST-17 strains, represented on the one hand by strain BM110 (for the strains having two copies of the S11 segment) and on the other hand by strain COH-1 or strain NEM318 (for the strains having only one copy of one S11 segment).

In a particular embodiment of the invention, the polynucleotide is disclosed with respect to its ability to hybridize with the gbs2018 gene as disclosed herein or to fragments thereof as defined in the application.

In a particular embodiment, the gbs2018 gene against which hybridization capacity is determined is one of the strand of the gene of strain NEM318 deposited at the CNCM under No I-3537.

In a particular embodiment, the fragment against which hybridization capacity is determined is the S10 fragment or the S11 fragment of the gene of strain NEM318 deposited at the CNCM under No I-3537 or a fragment complementary thereof.

In a particular embodiment, the fragment derived from the gbs2018 gene as defined in the present application, is defined as being suitable for use in a process for the detection, especially for the specific detection of a GBS strain of the ST-17 clone.

According to this embodiment, the strain as such is not necessarily detected but the process enables in vitro detection of an infection by such strain, especially by enabling direct or indirect detection of its DNA or of its polypeptidic products or antibodies directed against said products.

As used herein, "stringent conditions" refers to conditions of hybridization that pertains to the knowledge of the skilled person as defined, for example in Sambrook et al. (Sambrook et Russel. 2001. Molecular cloning: a laboratory manual, $3^{rd}$ ed., Cold Spring Harbor Laboratory Press, Cold Spring Harbor, N.Y). For illustration of such conditions suitable to perform the invention, "stringent conditions" correspond to the conditions allowing the specific hybridization of two single stranded DNA molecules after one "washing step". For instance, the hybridization can be conducted from about 35 to 65° C. using a salt solution, for example a solution comprising SSC 6×, SDS 0.5%, Denhardt's solution 5× and 100 µg of non-specific DNA, or in any other solution of equivalent ionic strength. The "washing step", comprising at least one wash, can be, for example, conducted at about 65° C. in a solution comprising at max 0.2×SSC and at max 0.1% SDS, or in any other solution of equivalent ionic strength. However, the skilled person will be able to vary such conditions as appropriate in order to take into account variables such as the length of polynucleotides sequences, the base composition, the type of ions present, etc.

The use of the fragment suitable in the process for the detection, especially for the specific detection of a ST-17 strain, can for example involve using a fragment which is a target for the detection, or a primer for elongation or amplification, or a probe for the detection, or an amplification or elongation product of the targeted gene sequence, as well as using a fragment which codes for a polypeptide of at least 6 amino acid, said polypeptide being recognized by an antibody according to the invention.

The expression "suitable for" means that the fragment relates to a polynucleotide which is selected and derived from particular regions of the gene gbs2018 of GBS strain that characterize the Sequence Type 17 strains of S. agalactiae or from a polynucleotide hybridizing under stringent conditions with, or complementary to, said gene or a fragment thereof. In a particular embodiment, said regions are not found in other strains such as those of serotype III which are not ST-17 strains, or those illustrated in Table S2 below. Accordingly polynucleotides suitable in a process for the detection of ST-17 strains, especially fragments of the gbs2018 gene are those which enable, in a specific process of detection, discrimination between ST-17 strains and other GBS strains of serotype III. Such polynucleotides provide tools for the design of detection processes having sensibility and specificity in accordance with requirements for diagnosis or for the determination of an infection due to an ST-17 strain. In a particular embodiment, such suitable polynucleotides enable the exclusive detection of ST-17 clones.

In an embodiment, the expression "suitable for" refers to fragments comprising whole or parts of the nucleic acid sequence of the segment S10 (FIG. 3b) of SEQ ID NO 5, or whole or parts of the nucleic acid sequence of the segment S11a (FIG. 4a) of SEQ ID NO 13 and/or the segment S11b (FIG. 4b) of SEQ ID NO 15, or sequences complementary to these sequences or hybridizing to any of these sequences in stringent conditions.

In a particular embodiment, the expression "suitable for" refers to fragments comprising whole or part of the nucleic acid sequence of the oligonucleotide ST-17S (Table S1) of SEQ ID NO 33, whole or part of the nucleic acid sequence of the oligonucleotide ST-17AS (Table S1) of SEQ ID NO 34, or whole or part of the nucleic acid sequence of the amplification product ST-17S/ST-17AS (FIG. 5a) of SEQ ID NO 35 obtained with the primer set consisting of ST-17S and ST-17AS, or sequences complementary to these sequences or hybridizing to any of these sequences in stringent conditions.

In another particular embodiment, the expression "suitable for" refers to fragments comprising whole or part of the nucleic acid sequence of the oligonucleotides O11 (Table S1) of SEQ ID NO 27, whole or part of the nucleic acid sequence of the oligonucleotide O12 (Table S1) of SEQ ID NO 28 or whole or part of the nucleic acid sequence of the oligonucleotide O13 (Table S1) of SEQ ID NO 29.

In a further particular embodiment, the expression "suitable for" refers to fragments comprising whole or part of the nucleic acid sequence of the amplification product O13/ST-17AS (FIG. 5b) of SEQ ID NO 36 obtained with the primer set consisting of O13 and ST17-AS, or sequences complementary to these sequences or hybridizing to any of these sequences in stringent conditions.

In another embodiment, the expression "suitable for" refers to fragments comprising whole or part of the nucleic acid sequence of the amplification product O13/O12 (FIG. 5c) of SEQ ID NO 37 obtained with the primer set consisting of O13 and O12, or sequences complementary to these sequences or hybridizing to any of these sequences in stringent conditions.

In a further embodiment, the expression "suitable for" refers to fragments comprising whole or part of the nucleic acid sequence of the amplification product ST-17S1012 (FIG. 5d) of SEQ ID NO 38, obtained with the primer set consisting of ST-17S and O12, or sequences complementary to these sequences or hybridizing to any of these sequences in stringent conditions.

In another embodiment, the expression "suitable for" refers to fragments comprising whole or part of the nucleic acid sequence of the amplification product O11/ST-17AS (FIG. 5e) of SEQ ID NO 39, obtained with the primer set consisting of O11 and ST17-AS, or sequences complementary to these sequences or hybridizing to any of these sequences in stringent conditions.

In a further embodiment, the expression "suitable for" refers to fragments comprising whole or part of the nucleic acid sequence of the amplification product O11/O12 (FIG. 5f) of SEQ ID NO 40, obtained with the primer set consisting of O11 and O12, or sequences complementary to these sequences or hybridizing to any of these sequences in stringent conditions.

As used herein, the term "specific" refers to the ability to detect GBS strains of Sequence Type 17 using the means detailed in the present invention. According to another particular embodiment of the present invention, the specific detection of GBS strains of ST-17 in a biological sample enables to discriminate said strain from other microorganisms comprising, for example, bacteria, viruses or parasites. In a further particular embodiment, GBS strains of ST-17 are detected whereas other Streptococcus strains are not and preferably the detection excludes that other GBS strains be detected in the sample.

A particular polynucleotide suitable to carry out the invention is the gbs2018 gene of sequence gbs2018-NEM318 (FIG. 1) having SEQ ID NO 1 or a fragment thereof as defined above, especially a fragment suitable for use in a process for the detection, especially the specific detection, of a GBS strain of the ST-17 clone.

Another polynucleotide of the invention is a fragment which is derived from the S10 segment in a gbs2018 gene in a strain of ST-17 clone.

In a particular embodiment, the polynucleotide is a fragment derived from the S10 segment that has the sequence S10 (FIG. 3b) of SEQ ID 5. Especially, this fragment is chosen in such a way that it is suitable for use in a process for the detection, especially the specific detection, of a GBS strain of the ST-17 clone.

A particular polynucleotide of the invention is a DNA fragment derived from the gene defined in the application, and having at least 10, especially 10 to 30, especially at least 15, for example 15 to 30, especially at least 20, for example 20 to 30, or 20 to 25 nucleotides. Any specific size within the ranges defined above is encompassed within the frame of the invention, or any range build from the above figures.

Another particular polynucleotide of the invention is a DNA fragment derived from said gene, having 10 to 700, especially at least 50, for example 50 to 700 or at least 100, especially 100 to 500, in particular at least 200, for example 200 to 500, or 200 to 300 nucleotides. Any specific size within the ranges defined above is encompassed within the frame of the invention, or any range build from the above figures. Such polynucleotides are especially amplification products obtained with the oligonucleotides disclosed in the invention, used as amplification primers.

The invention especially relates to a fragment which is selected among:
  a) a polynucleotide having SEQ ID NO 33;
  b) a polynucleotide having SEQ ID NO 34;
  c) a polynucleotide having SEQ ID NO 27;
  d) a polynucleotide having SEQ ID NO 28;
  e) a polynucleotide having SEQ ID NO 29;
  f) a polynucleotide which is the amplification product obtained when amplifying DNA of a GBS strain with a primer set consisting of SEQ ID NO 33 and SEQ ID NO 34, especially a polynucleotide consisting of SEQ ID NO 35;
  g) a polynucleotide which is the amplification product obtained when amplifying DNA of a GBS strain with a primer set consisting of SEQ ID NO 29 and SEQ ID NO 34, especially a polynucleotide consisting of SEQ ID NO 36;
  h) a polynucleotide which is the amplification product obtained when amplifying DNA of a GBS strain with a primer set consisting of SEQ ID NO 29 and SEQ ID NO 28, especially a polynucleotide consisting of SEQ ID NO 37;
  i) a polynucleotide which is the amplification product obtained when amplifying DNA of a GBS strain with a primer set consisting of SEQ ID NO 33 and SEQ ID NO 28, especially a polynucleotide consisting of SEQ ID NO 38;
  j) a polynucleotide which is the amplification product obtained when amplifying DNA of a GBS strain with a primer set consisting of SEQ ID NO 27 and SEQ ID NO 34, especially a polynucleotide consisting of SEQ ID NO 39;
  k) a polynucleotide which is the amplification product obtained when amplifying DNA of a GBS strain with a primer set consisting of SEQ ID NO 27 and SEQ ID NO 28, especially a polynucleotide consisting of SEQ ID NO 40;
  l) a polynucleotide which is substantially complementary to one strand of one of polynucleotides a) to k);
  m) a polynucleotide which hybridises in stringent conditions with the polynucleotide of l);
  n) a polynucleotide which is suitable for targeting a gbs2018 gene of the ST-17 clone or a fragment thereof, for the amplification and/or the detection of a sequence comprising or consisting of the S10 and/or the S11 segments of said gene.

A particular polynucleotide fragment of the invention is derived from segment designated S11 in a gbs2018 gene, of a strain of ST-17 clone.

In a particular aspect of the invention, the S11 region has the sequence S11a (FIG. 4a) of SEQ ID NO 13 and/or the sequence S11b (FIG. 4b) of SEQ ID NO 15.

The invention also relates to a primer set, suitable for use in a process for the detection of DNA of a GBS strain of ST-17 clone or for the detection of products derived from such DNA, wherein said primer set comprises or consists in the following primer pairs:
  a) ST-17S having sequence of SEQ ID NO 33 and ST-17AS having sequence of SEQ ID NO 34;
  b) ST-17S having sequence of SEQ ID NO 33 and O12 having sequence of SEQ ID NO 28;
  c) O11 having sequence of SEQ ID NO 27 and O12 having sequence of SEQ ID NO 28;
  d) O12 having sequence of SEQ ID NO 28 and O13 having sequence of SEQ ID NO 29;
  e) O11 having sequence of SEQ ID NO 27 and ST-17AS having sequence of SEQ ID NO 34;
  f) O13 having sequence of SEQ ID NO 29 and ST-17AS having sequence of SEQ ID NO 34;
  g) primer pairs which are substantially complementary to primers in a) to f);
  h) primer pairs wherein each polynucleotide is suitable for targeting a gbs2018 gene of the ST-17 clone or a fragment thereof, for the amplification of a sequence comprising or consisting of the S10 and/or the S11 segments of said gene.

In a particular embodiment, the primer pair consists of ST-17S having the sequence of SEQ ID NO 33 and ST-17AS having sequence of SEQ ID NO 34.

In a further embodiment, the primer pair consists of ST-17S having the sequence of SEQ ID NO 33 and O12 having sequence of SEQ ID NO 28.

In a further embodiment, the primer pair consists of O11 having the sequence of SEQ ID NO 27 and O12 having sequence of SEQ ID NO 28.

In a further embodiment, the primer pair consists of O12 having the sequence of SEQ ID NO 28 and O13 having sequence of SEQ ID NO 29.

In a further embodiment, the primer pair consists of O11 having the sequence of SEQ ID NO 27 and ST-17AS having sequence of SEQ ID NO 34.

In a further embodiment, the primer pair consists of O13 having the sequence of SEQ ID NO 29 and ST-17AS having sequence of SEQ ID NO 34.

In a further embodiment, the primer pair consists of O13 having the sequence of SEQ ID NO 27 and 08 having sequence of SEQ ID NO 24.

The term "primers" refers to a short polynucleotide that can be used in an amplification reaction, thereby rendering possible the amplification. Primers usually possess a sequence which is complementary to the extremities of the polynucleotide sequence to be amplified. Generally speaking, in the case of a sense primer, a larger number of mutations is tolerated at the 5' end than at the 3' end of the primer, the 3' end being required to hybridize perfectly with a specific strand of a nucleotide sequence in order for this sequence to be amplified. In the case of an anti-sense primer, it is at the 3' end that tolerance is allowed. In a particular embodiment, the amplification does not give rise to the presence of many aspecific bands. Increasing the length of the primers as well as using drastic conditions of amplification increases the specificity of hybridization, thereby making it possible to eliminate parasitic bands.

In a specific embodiment, the primers are selected in whole or parts of the gene gs2018 of a GBS strain of the ST-17 clone especially of the strain deposited at the CNCM under No I-3537. Primers are preferably a fragment of the gene gbs2018 of this strain, and more preferably a fragment of the segment S10 or of the segment S11 of said gene. Primers usually have a size ranging from 10 to 30, preferably from 15 to 30, more preferably from 20 to 30 and still more preferably from 20 to 25 nucleotides. In a preferred embodiment of the present invention, primers are selected among the following: ST-17S of SEQ ID NO 33, ST-17AS of SEQ ID NO 34, O11 of SEQ ID NO 27, O12 of SEQ ID NO 28 and O13 of SEQ ID NO 29.

The invention also concerns an amplification product (amplimer or amplicon) consisting of the product of the amplification of a DNA of a GBS strain of the ST-17 clone with a primer set according to the invention or comprising said product.

As used therein, "amplification product" refers to a polynucleotide obtained by any known methods including, but not limited to, any chemical method, any synthetic method, any recombinant method, any ex vivo generation method and the like, as well as combinations thereof. In a specific embodiment, these methods may comprise cloning, amplification or chemical synthesis.

In a particular embodiment, the "amplification product" refers to the polynucleotide selected between the following:

the polynucleotide of sequence ST-17S/ST-17AS (FIG. 5a) of SEQ ID NO 35, obtained with the primer set consisting of ST-17S of SEQ ID NO 33 and ST-17AS of SEQ ID NO 34;

the polynucleotide of sequence O13/ST-17AS (FIG. 5b) of SEQ ID NO 36 obtained with the primer set consisting of O13 of SEQ ID NO 29 and ST17-AS of SEQ ID NO 34;

the polynucleotide of sequence O13/O12 (FIG. 5c) of SEQ ID NO 37 obtained with the primer set consisting of O13 of SEQ ID NO 29 and O12 of SEQ ID NO 28;

the polynucleotide of sequence ST-17S/O12 (FIG. 5d) of SEQ ID NO 38, obtained with the primer set consisting of ST-17S of SEQ ID NO 33 and O12 of SEQ ID NO 28;

the polynucleotide of sequence O11/ST-17AS (FIG. 5e) of SEQ ID NO 39, obtained with the primer set consisting of O11 of SEQ ID NO 27 and ST17-AS of SEQ ID NO 34;

the polynucleotide of sequence O11/O12 (FIG. 5f) of SEQ ID NO 40, obtained with the primer set consisting of O11 of SEQ ID NO 27 and O12 of SEQ ID NO 28.

In a preferred embodiment, "amplification product" refers to the polynucleotide of sequence ST-17S/ST-17AS (FIG. 5a) of SEQ ID NO 35, obtained after PCR amplification with the oligonucleotides ST-17S of SEQ ID NO 33 and ST-17AS of SEQ ID NO 34.

The invention also relates to a recombinant or a chimeric polynucleotide which comprises a polynucleotide according to the invention and a heterologous polynucleotide. A heterologous polynucleotide is one which is not naturally associated with the polynucleotide of the invention. It is especially a polynucleotide derived from another region of the gbs2018 gene or from another gene of a GBS strain, or from another source.

The polynucleotides can be labelled in any manner suitable to enable their recognition. Means for labelling includes also insertion of nucleotides for detection.

The invention also relates to a kit for the in vitro detection of an infection by a GBS strain in a biological sample, which comprises a primer set as defined and means for the detection of the amplification product obtained with said primer set.

A particular kit of the invention further comprises a primer set suitable for the amplification of the DNA of GBS strains, said primer set comprising or consisting in at least two oligonucleotides, wherein at least one oligonucleotide is a sense primer and at least one oligonucleotide is an antisense primer, said oligonucleotides being selected between the following:

dltRS having sequence of SEQ ID NO 31;
dltRAS having sequence of SEQ ID NO 32;
O1 having sequence of SEQ ID NO 17;
O2 having sequence of SEQ ID NO 18;
O3 having sequence of SEQ ID NO 19;
O4 having sequence of SEQ ID NO 20;
O5 having sequence of SEQ ID NO 21;
O6 having sequence of SEQ ID NO 22;
O7 having sequence of SEQ ID NO 23;
O8 having sequence of SEQ ID NO 24;
O9 having sequence of SEQ ID NO 25;
O10 having sequence of SEQ ID NO 26;
O14 having sequence of SEQ ID NO 30;

As used herein, the term "kit" refers to a set of elements that are appropriate for the detection of an infection by a GBS strain of the ST-17 clone in a biological sample. In particular, a kit according to the invention comprises at least all the elements that are necessary and sufficient to allow the detection of ST-17 GBS strains such as, for example, one or more isolated polynucleotide sequences according to the invention, as well as the suitable reagents required for the implementation of the detection operation.

In a particular embodiment, detection is achieved through an amplification operation and said reagents comprise, but are not limited to, a DNA polymerase, the four different nucleosides triphosphates and the reaction medium. In a preferred embodiment, the kit comprises at least one set of primers according to the invention corresponding to those defined above.

In another embodiment, the kit comprises at least one probe corresponding to a polynucleotide of the invention, which probe can be a cold probe or can be labelled, in particular by radioactivity, and is capable of hybridizing specifically in the labelled or unlabelled form with the nucleic acid sequence(s) to be detected.

In a specific embodiment, the probe is selected in whole or parts of the gbs2018 gene of a GBS strain of the ST-17 clone. The probe is preferably a fragment of the gbs2018 gene of a GBS strain of the ST-17 clone, and more preferably a fragment of the segment S10 or of the segment S11 of said gene. The probe usually has a size ranging from 10 to 700, especially from 50 to 700, or alternatively from 10 to 50 or from 10 to 100, or from 100 to 500, or from 200 to 500 or still from 200 to 300 nucleotides.

In a particular embodiment of the present invention, the probe is selected among the following polynucleotides: ST-17S of SEQ ID NO 33, ST-17AS of SEQ ID NO 34, O11 of SEQ ID NO 27, O12 of SEQ ID NO 28 and O13 of SEQ ID NO 29.

In a preferred embodiment, the kit may comprise at least one positive and/or one negative controls allowing the user to check the validity of the detection result. For instance, a negative control can include, but is not limited to, water, buffer, or any non-ST-17 GBS micro-organism, such as bacteria, viruses or parasites, or nucleic acid sequences thereof. By "non-ST-17 organism", it is meant an organism that is not identified as a GBS strain of the ST-17 clone using known methods of detection including culture methods or molecular methods such as multilocus enzyme electrophoresis (MLEE), multilocus sequencing typing (MLST), pulse-field gel electrophoresis (PFGE), restriction digest pattern, restriction fragment length polymorphism (RFLP) and the like, as well as combinations thereof.

A positive control can include, but is not limited to, any polynucleotide of the invention as defined above as well as any organism containing the polynucleotide of the invention.

Optionally, the kit may further comprise the elements necessary for the sampling of biological samples such as, for example, extraction tools like needles and syringes, collection containers or the like, and combinations thereof, and possibly directions for use. By biological sample, it is meant any sample collected from a biological organism, preferably from a mammalian organism, more preferably from a human organism and most preferably from a pregnant-woman organism or a neonate. In a preferred embodiment, the biological sample is a body fluid such as serum, blood or mucosal secretions, like, for example, secretions originating from mucosal membranes such as nasal, oral, gastro-intestinal, vaginal or anal membranes.

Optionally, the kit may further comprise the elements necessary for the detection of PCR amplification products. For instance, PCR products can be detected with the use of a standard intercalant agent, such as BET or SYBR green, after separation by agarose gel electrophoresis [Huang et al., 2005]. In a further embodiment, amplification products are obtained by real-time PCR and are detected with non-specific fluorescent intercalant agents, such as SYBR green [Whitcombe D et al., 1999]. In another embodiment, amplification products are obtained by real-time PCR and are detected through the use of specific fluorescent probes, such as, for example, the Taqman system [Holland P M et al., 1991], the Molecular Beacon system [Tyagi S et al., 1996], or the FRET (Fluorescence resonance energy transfer) system [Wittwer C T et al., 1997].

The invention also concerns a process for the in vitro detection of a high-virulence GBS strain of the ST-17 clone which comprises detecting the gbs2018 gene or fragments thereof, or DNA products derived from said gene, in a biological sample. In a particular embodiment, said process comprises detecting the S10 segment and/or S11 segment in gbs2018 gene.

A particular process for the detection is one which comprises a step of amplification of the gbs2018 gene or of specific fragment(s) thereof or of DNA product(s) derived from said gene.

A particular process for the detection is one which comprises a step of elongation of the gbs2018 gene or of specific fragment(s) thereof or of DNA product(s) derived from said gene.

In such process, the step of amplification or the step of elongation involves using a primer set preferably comprising or consisting of at least one of the following primer pairs:
 a) ST-17S having sequence of SEQ ID NO 33 and ST-17AS having sequence of SEQ ID NO 34;
 b) O1 having sequence of SEQ ID NO 17 and O12 having sequence of SEQ ID NO 28;
 c) O11 having sequence of SEQ ID NO 27 and O12 having sequence of SEQ ID NO 28;
 d) O13 having sequence of SEQ ID NO 29 and O8 having sequence of SEQ ID NO 24;
 e) O9 having sequence of SEQ ID NO 25 and O14 having sequence of SEQ ID NO 30;
 f) O9 having sequence of SEQ ID NO 25 and O2 having sequence of SEQ ID NO 18;
 g) ST-17S having sequence of SEQ ID NO 33 and O12 having sequence of SEQ ID NO 28;
 h) O12 having sequence of SEQ ID NO 28 and O13 having sequence of SEQ ID NO 29;
 i) O11 having sequence of SEQ ID NO 27 and ST-17AS having sequence of SEQ ID NO 34;
 j) O13 having sequence of SEQ ID NO 29 and ST-17AS having sequence of SEQ ID NO 34;
 k) primer pairs which are substantially complementary to primers in a) to j);
 l) primer pairs wherein each polynucleotide is suitable for targeting a gbs2018 gene of the ST-17 clone or a fragment thereof, for the amplification of a sequence comprising or consisting of the S10 and/or the S11 segments of said gene, or a fragment of said segments.

In a particular embodiment of said process, the step of amplification or the step of elongation involves using a primer set consisting of ST-17S having sequence of SEQ ID NO 33 and ST-17AS having sequence of SEQ ID NO 34.

In a particular aspect of the invention, the amplification is carried out by PCR. Other amplification methods can be used, for example SDA, SSSR, LCR, TMA, NASBA etc. . . .

As used herein, the term "amplification" refers to the multiplication of a target polynucleotide sequence by any known methods including, but not limited to, any chemical method, any synthetic method, any recombinant method, any ex vivo generation method and the like, as well as combinations thereof. In a specific embodiment, these methods of amplification may comprise cloning, PCR amplification or chemical synthesis.

In a preferred embodiment, the amplification refers to PCR amplification of the targeted polynucleotide sequences. Said PCR amplification is based on a cycle comprising the following steps:

denaturation of the double stranded nucleic acid to be detected, which leads to the formation of a single stranded nucleic acid, hybridization of each of the strands of the nucleic acid obtained during the previous denaturation step with at least one primer according to the invention, by placing the strands of said nucleic acid in contact with at least one set of primers according to the invention under stringent hybridization conditions, formation, starting from the primers, of the DNA complementary to the strands to which primers are hybridized in presence of a polymerization agent (DNA polymerase) and the four different nucleoside triphosphates (dNTPs).

Consecutive repetitions of the above cycle lead to the formation of a greater number of double-stranded nucleic acids to be detected than in the previous denaturation step. The cycle is repeated a defined number of times in order to obtain the amplified targeted polynucleotide sequence in an amount sufficient to allow its detection.

The agent of polymerization used in the elongation step of the cycle is a thermostable DNA polymerase, in particular a Taq polymerase or any polymerase which is commercially available.

It is obvious that the conditions mentioned in the examples may be modified, depending for example on the origin of the biological sample, the length and sequence of the primers, or the final volume of the reaction mixture.

The process for the detection requires identification of the DNA of high-virulence GBS strains of the ST-17 clone or identification of DNA fragments thereof, or of products derived from said DNA, as a result of the implementation of the process for the detection of the invention. Means enabling the accurate discrimination between the organisms (or nucleic acids thereof) containing the allelic form of the gene gbs2018 specific for the ST-17 strain, and other strains and/or organisms (or nucleic acids thereof) are preferred. In a particular embodiment of the invention, the term "detection" refers to the specific identification of the infection due to GBS strains of the ST-17 clone from a biological sample, and, in a more particular embodiment, detection enables to discriminate strains of the ST-17 clone from other *Streptococcus* strains and preferably amongst other GBS strains of serotype III. In a still more preferred embodiment, GBS strains of the ST-17 clone are exclusively detected, without allowing the detection of other sequence type GBS strains, neither other *Streptococcus* strains nor other microorganisms.

In a specific embodiment of the invention, the detection may comprise an amplification operation of whole or part of the allelic form of the gbs2018 gene which is specific from GBS strains of the ST-17 clone, such as, in particular, the nucleic acid sequences of the segments S10 of sequence S10 (FIG. 3b) of SEQ ID NO 5, S11a of sequence S11a (FIG. 4a) of SEQ ID NO 13 and/or S11b of sequence S11b (FIG. 4b) of SEQ ID NO 15, or fragments thereof. Said amplification operation may comprise any known methods including, but not limited to, any chemical method, any synthetic method, any recombinant method, any ex vivo generation method and the like, as well as combinations thereof. In a specific embodiment, these methods of amplification may comprise cloning, PCR amplification or chemical synthesis.

In another embodiment, the detection may comprise an hybridization operation with a probe made of a polynucleotide of the invention or derived therefrom. In particular, a probe can be prepared from whole or part of the allelic form of the gbs2018 gene which is specific from GBS strains of the ST-17 clone, such as, in particular, the nucleic acid sequences of the segments S10 of sequence S10 (FIG. 3b) of SEQ ID NO 5, S11a of sequence S11a (FIG. 4a) of SEQ ID NO 13 or S11b of sequence S11b (FIG. 4b) of SEQ ID NO 15, or fragments thereof, or fragments of the gene comprising said S10 and/or S11 segments or fragments of said segments. Said hybridization operation mainly comprises the steps consisting in: denaturing the targeted nucleic acids to be detected, contacting the probe with the denatured nucleic acids, recovering the hybrids obtained, for example by a washing step to remove aspecific associations. The conditions of hybridization are those defined in the present application, either above or in the examples.

The process for detection can also comprise means and steps for visualizing the result of the amplification operation or of the hybridization operation. Said visualization means are well known by the person skilled in the art and can include, but are not limited to, chemical, enzymatical or biological labelling means and means capable of identifying chemical, enzymatical or biological labelling, as, for example, cold labelling, radioactive labelling and fluorescence labelling.

In a specific embodiment of the invention, the detection process may optionally comprise the extraction, the separation, the preparation, the purification, and the like, of a biological sample. In particular, the detection may comprise an optional step involving the extraction of the nucleic acids to be detected that are contained into the biological sample. If appropriate, the extraction/purification step can also involve the incubation of the said nucleic acid with a reverse transcriptase if this latter is in the form of RNA.

The invention also relates to a polypeptide encoded by one of the polynucleotides of the invention defined herein. In a particular embodiment, this polypeptide is not the one having the sequence Gbs2018-NEM318 (FIG. 1) of SEQ ID NO 2. The invention nevertheless comprises the fragments of said polypeptide encoded by one of the polynucleotides of the invention, and the use of the polypeptide or of the fragments thereof, as defined in the present application.

A particular polypeptide is a fragment having at least 6 amino acid residues, especially a fragment comprising epitope(s) of the Gbs2018 surface protein of a strain of the ST-17 clone. In a particular embodiment, the fragment is a fragment of the Gbs2018 surface protein of a strain of the ST-17 clone having sequence Gbs2018-NEM318 (FIG. 1) of SEQ ID NO 2.

According to an embodiment the polypeptide is derived from the polypeptidic region designated S10 in the Gbs2018 protein in GBS strains of the ST-17 clone and is selected among:
 the polypeptide S10 segment, especially the polypeptide having sequence S10 (FIG. 3b) of SEQ ID NO 6;
 a fragment thereof, especially a fragment having at least 6 amino acid residues and containing an epitope;
 a polypeptide comprising said S10 segment and having at least 190 amino acid residues and less than 550 or less than 300 or less than 250 amino acid residues.

A particular fragment of the S10 polypeptidic region that has the sequence S10 (FIG. 3b) of SEQ ID NO 6, is one which is recognized by antibodies directed or raised against the Gbs2018 surface protein.

According to an embodiment the polypeptide is derived from the polypeptidic region designated S11 in the Gbs2018 protein in GBS strains of the ST-17 clone and is selected among:
 the polypeptide S11a segment, especially the polypeptide having sequence S11a (FIG. 4a) of SEQ ID NO 14;
 the polypeptide S11b segment, especially the polypeptide having sequence S11b (FIG. 4b) of SEQ ID NO 16;
 a fragment thereof, especially a fragment having at least 6 amino acid residues and containing an epitope;
 a polypeptide comprising said S11a segment and having at least 72 amino acid residues and less than 550 or less than 300 or less than 250 amino acid residues;
 a polypeptide comprising said S11b segment and having at least 79 amino acid residues and less than 550 or less than 300 or less than 250 amino acid residues.

A particular fragment of the S11a polypeptidic region that has the sequence S11a (FIG. 4a) of SEQ ID NO 14, is one which is recognized by antibodies directed or raised against the Gbs2018 surface protein.

A particular fragment of the S11b polypeptidic region that has the sequence S11b (FIG. 4b) of SEQ ID NO 16, is one which is recognized by antibodies directed or raised against the Gbs2018 surface protein.

Polypeptides of the invention can comprise an epitope and have 6 to 50, or 6 to 30, or 6 to 15 amino acids, which polypeptide possess the ability of being recognized by antibodies directed to the Gbs2018 surface protein.

In a particular embodiment the polypeptide is derived from a strain of the ST-17 clone and is not recognized by antibodies raised against the Gbs2018 surface protein of other strains of serotype III of GBS.

The invention also relates to a recombinant or a chimeric polypeptide comprising a polypeptide as defined herein and a heterologous polypeptide. A heterologous polypeptide is one which is not naturally associated with the polypeptide of the invention. It is especially a polypeptide derived from another region of the Gbs2018 surface protein or from another surface protein of a GBS strain, or from another source.

The polypeptide of the invention can be in association with a carrier molecule.

The invention also concerns antibodies characterized in that they recognize the GBS surface protein of the ST-17 clone of GBS strains, in particular said surface protein having the sequence Gbs2018-NEM318 (FIG. 1) of SEQ ID NO 2, or a fragment thereof comprising the S10 segment and/or S11 segment. Such fragments have been defined hereabove. Especially, these antibodies recognize the above polypeptides with a higher affinity than other GBS surface proteins of other GBS strains, or do not recognize such other GBS surface proteins.

The invention also relates to a process for the preparation of antibodies against a polypeptide as defined herein, which process comprises immunizing an animal with said polypeptide and recovering the antibodies raised against said polypeptide.

The invention also relates to a monoclonal antibody directed against a polypeptide as defined herein, said monoclonal antibody recognizing specifically the GBS surface protein of the clone ST-17 of GBS strains, and, in particular, a fragment thereof comprising whole or part of the S10 segment and/or S11 (S11a and/or S11b) segment. Such fragments have been defined hereabove.

The invention also concerns fragments of herein defined antibodies, including fragments comprising or consisting of whole or part of the variable domain sufficient for recognizing and binding said GBS surface protein.

The invention also relates to the use of the polypeptides defined herein, including the use of the Gbs2018-NEM318 (FIG. 1) polypeptide and fragments thereof, for the applications defined herein, especially for in vitro detection of an infection by a GBS strain, in particular of ST-17 clone, in a biological sample.

A kit for the in vitro detection of an infection by a GBS strain in a biological sample, comprising a polypeptide of the invention or an antibody according to the invention or a fragment thereof, and means for the detection of the antigen/antibody complex obtained with said polypeptide or said antibody or fragments thereof and the biological sample is also encompassed in the invention.

The polynucleotides, polypeptides, antibodies and fragments thereof, process, kits according to the invention are suitable for use in the detection of a strain of the ST-17 clone of GBS strains in mammals and/or in humans.

Polynucleotides, polypeptides, antibodies and fragments thereof, process, kits according to the invention are especially suitable for use in the detection of a strain of the ST-17 clone of GBS strains in pregnant woman, in embryo, in foetus, in neonates and/or a child.

The polynucleotides, polypeptides, antibodies and fragments thereof, process, kits disclosed in the present invention are means for use in the detection of neonatal invasive infections, neonatal mortality or neonatal morbidity caused by a strain of the ST-17 clone of GBS strains.

In particular, polynucleotides, polypeptides, antibodies and fragments thereof, process, kits according to the invention are suitable for use in the detection of newborn pneumonia, bacteraemia or meningitis caused by the ST-17 clone of GBS strains.

Other characterizing features of the invention will become apparent from the examples and from the figures and they apply, individually or in combination, to the above disclosed elements of the invention.

BRIEF DESCRIPTION OF THE DRAWINGS

The following figures are provided for illustration and should not be considered as limiting the object of the present invention.

FIGS. 1A and B is the nucleic sequence and corresponding amino acid sequence of the gbs2018 gene of the ST-17 strain NEM318. The first line indicates the nucleotide sequence, grouped by codons; the second line indicates the amino acid sequence corresponding to the above codons with the three-letter code. The first codon of translation is shown in bold as well as the stop codon. Numbering of the nucleic acids is at the right end of the first line, whereas numbering of the amino acids is indicated under amino acid residue (third line). The nucleic sequence (of SEQ ID NO 1) of the coding sequence of the gbs2018-NEM318 gene contains 1569 nucleotides and encodes a polypeptidic sequence (of SEQ ID NO 2) of 522 amino acids.

FIG. 2A-C is the nucleic sequence and corresponding amino acid sequence of the segments S1 (FIG. 2a), S6 (FIG. 2b) and S7 (FIG. 2c) of the gbs2018 gene of ST-17 strains. The first line indicates the nucleotide sequence, grouped by codons; the second line indicates the amino acid sequence corresponding to the above codons with the three-letter code. Numbering of the nucleic acids is at the right end of the first line, whereas numbering of the amino acids is indicated under amino acid residue (third line). The nucleic sequence (of SEQ ID NO 3) of segment S1 contains 99 nucleotides and encodes a polypeptidic sequence (of SEQ ID NO 4) of 33 amino acids. The nucleic sequence (of SEQ ID NO 7) of segment S6 contains 291 nucleotides and encodes a polypeptidic sequence (of SEQ ID NO 8) of 97 amino acids. The nucleic sequence (of SEQ ID NO 9) of segment S7 contains 180 nucleotides and encodes a polypeptidic sequence (of SEQ ID NO 10) of 60 amino acids.

FIG. 3A-B is the nucleic sequence and corresponding amino acid sequence of segments S8 (FIG. 3a) and S10 (FIG. 3b) of the gbs2018 gene of ST-17 strains. The first line indicates the nucleotide sequence, grouped by codons; the second line indicates the amino acid sequence corresponding to the above codons with the three-letter code. Numbering of the nucleic acids is at the right end of the first line, whereas numbering of the amino acids is indicated under amino acid residue (third line). The nucleic sequence (of SEQ ID NO 11) of segment S8 contains 192 nucleotides and encodes a polypeptidic sequence (of SEQ ID NO 12) of 63 amino acids. The nucleic sequence (of SEQ ID NO 5) of segment S10 contains 570 nucleotides and encodes a polypeptidic sequence (of SEQ ID NO 6) of 190 amino acids.

FIG. 4A-B is the nucleic sequence and corresponding amino acid sequence of the segments S11a (FIG. 4a) and S11b (FIG. 4b) of the gbs2018 gene of ST-17 strains. The first line indicates the nucleotide sequence, grouped by codons; the second line indicates the amino acid sequence corresponding to the above codons with the three-letter code. Numbering of the nucleic acids is at the right end of the first line, whereas numbering of the amino acids is indicated under amino acid residue (third line). The nucleic sequence (of SEQ ID NO 13) of segment S11a contains 216 nucleotides and encodes a polypeptidic sequence (of SEQ ID NO 14) of 72 amino acids. The nucleic sequence of segment S11b (of SEQ ID NO 15) contains 237 nucleotides and encodes a polypeptidic sequence (of SEQ ID NO 16) of 79 amino acids.

FIG. 5A-F corresponds to the nucleic acids sequences of the amplification products obtained with different primer sets of the invention. The nucleic acid sequence (of SEQ ID NO 35) ST-17S/ST-17AS (208 nucleotides) corresponds to the amplification product obtained with primers ST-17S of SEQ ID NO 33 and ST-17AS of SEQ ID NO 34 (FIG. 5a). The nucleic acids sequence (of SEQ ID NO 36) O13/ST-17AS (101 nucleotides) corresponds to the amplification product obtained with primers O13 of SEQ ID NO 29 and ST-17AS of SEQ ID NO 34 (FIG. 5b). The nucleic acids sequence (of SEQ ID NO 37) O13/O12 (107 nucleotides) corresponds to the amplification product obtained with primers O13 of SEQ ID NO 29 and O12 of SEQ ID NO 28 (FIG. 5c). The nucleic acids sequence (of SEQ ID NO 38) ST-17S/O12 (214 nucleotides) corresponds to the amplification product obtained with primers ST-17S of SEQ ID NO 33 and O12 of SEQ ID NO 28 (FIG. 5d). The nucleic acids sequence (of SEQ ID NO 39) O11/ST-17AS (543 nucleotides) corresponds to the amplification product obtained with primers O11 of SEQ ID NO 27 and ST-17AS of SEQ ID NO 34 (FIG. 5e). The nucleic acids sequence (of SEQ ID NO 40)

O11/O12 (549 nucleotides) corresponds to the amplification product obtained with primers O11 of SEQ ID NO 27 and O12 of SEQ ID NO 28 (FIG. 5f).

Figure 6:
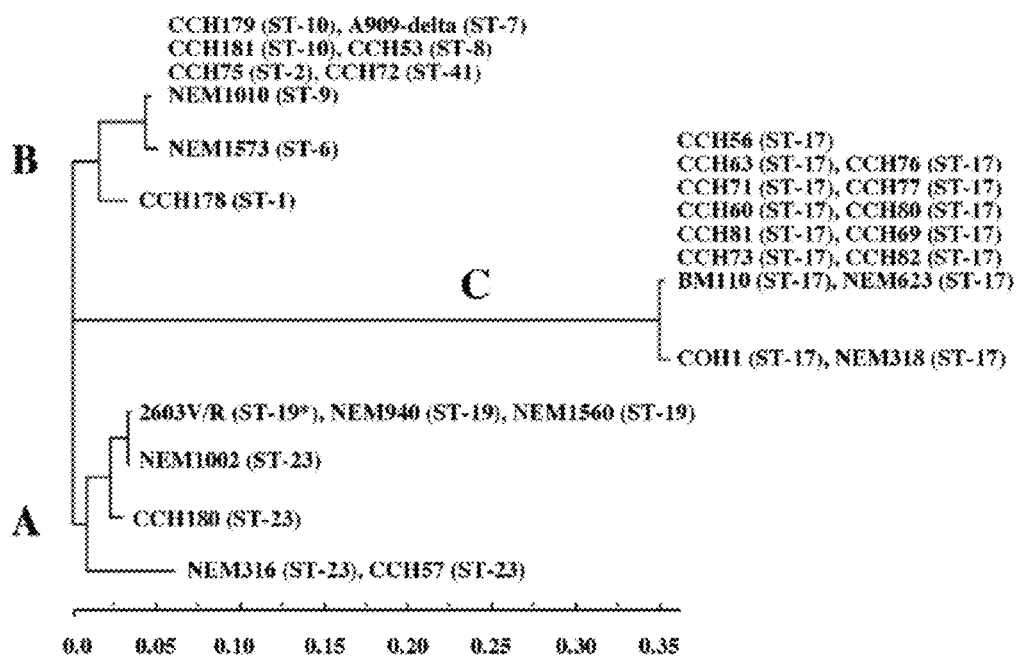

FIG. 6: Phylogenetic tree of genes encoding different chimeric forms of the Gbs2018 surface protein in 31 GBS isolates belonging to different sequence types (ST). Alignment and comparison of the DNA sequences of GBS isolates has revealed a three-ways lineage, thereby classifying the gbs2018 allelic forms in three clusters (A, B and C). The percentage sequence divergence is indicated below the tree.

Figure 7:
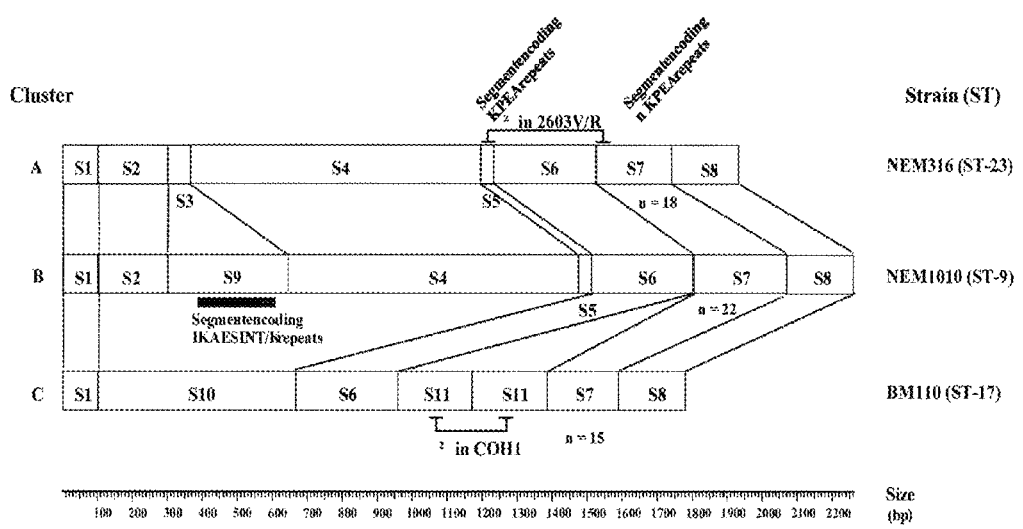

FIG. 7: Mosaic structure of the genes encoding the three allelic forms of the surface protein Gbs2018. Representative members of each phylogenetic cluster (A, B, and C; defined in FIG. 5) are presented.

FIG. 8A-B: Specific detection of ST-17 among GBS isolates. GBS strains were identified by PCR amplifications using primer pairs dltRS/dltRAS (specific for dltR, 234-pb amplicon). Primers ST-17S/ST-17AS (specific for gbs2018-ST-17, 210-bp amplicon) were used to discern ST-17 strains. In panel A, the ten samples tested were GBS strains of serotype III belonging to the ST-17 clonal complexe: 1, BM110; 2, COH1; 3, NEM318; 4, CCH56; 5, CCH63; 6, CCH80; 7, CCH76; 8, CCH77; 9, CCH81; 10, CCH82. In panel B, the ten GBS strains tested were of different serotypes and belonged to various ST: 1, NEM316 (serotype III, ST-23); 2, GBS 2603V/R (serotype V, ST-19*); 3, CCH178 (serotype V, ST-1); 4, CCH75 (serotype III, ST-2); NEM1573 (serotype Ia, ST-6); CCH53 (serotype Ib, ST-8); NEM1010 (serotype II, ST-9); CCH179 (serotype II, ST-10); CCH180 (serotype I, ST-23); CCH72 (serotype III, ST-41). The molecular weight marker 1 kb Ladder-Plus (Gibco-BRL) was loaded in lane M.

EXAMPLES

The following examples and corresponding figures are provided to illustrate the present invention, and should not be considered as limitations to the scope of the invention. In the same way, the specific means disclosed in the examples are suitable to apply to the above described elements.

Example 1

Identification, Serotyping and DNA Extraction of the GBS Strains

In order to characterize the genetic diversity of the gbs2018 gene, 181 unrelated GBS strains including the three sequenced strains NEM316 serotype III, 2603V/R serotype V, strain A909 serotype Ib (tigr.org/tdb/mdb/mdbinprogress.html), the partially sequenced serotype III strain COH1 and the well-characterized serotype III strain BM110 were studied.

As it is detailed in the table 1 presented below, the collection included 155 human strains from various France geographical origins isolated between 1990 and 2005, 8 strains from various UK geographical origins and 13 bovine mastitis strains.

GBS strain identification was realized using a commercial latex agglutination test (bio Mérieux, Marcy l'Etoile, France), and the strains were serotyped by agglutination using a commercial kit from Essum Corporation (Umea, Sweden). All GBS strains were grown on Columbia agar containing 5% of horse blood at 37° C. under a 5% CO2 atmosphere, and the corresponding stock cultures were stored frozen at −80° C. in Todd-Hewitt broth containing 10% glycerol.

DNA was extracted from bacterial cultures and clinical samples of sixteen clinical isolates representative of different STs.

Total DNA extraction from overnight bacterial colonies was carried out by using the InstaGene™ Matrix (Bio-Rad, Hercules, Calif.).

DNA from vaginal samples was extracted as described in Reglier-Poupet et al., 2005. Briefly, secretions of the mucosa of the lower third of the vagina were obtained with a cotton swab. The same specimen was used for the standard culture and the PCR assay. The swab was discharged and vortexed in 500 µl of sterile PBS. For microbiological cultures and identification of GBS, 100 µl was inoculated on Columbia horse blood agar plates and incubated at 37° C. under 5% CO2 for 18 h. β-Hemolytic colonies and suspected non-hemolytic colonies were identified as GBS by using a commercial latex agglutination test (bioMérieux). For PCR assays, the remaining 400 µl was immediately frozen at −80° C. until extraction. One hundred microliters of the frozen sample was prepared as a crude lysate using a commercial DNA extraction kit according to the manufacturer's protocol (QIAamp DNA minikits, Qiagen Courtaboeuf, France).

TABLE 1

Origin and serotype of GBS isolates used in this study[a]

| Origin of GBS strains[b] | | No of isolates of serotype | | | | | | |
|---|---|---|---|---|---|---|---|---|
| | | Ia | Ib | II | III | IV | V | NT |
| No of strains (%) Human origin | 176 | 18 | 11 | 12 | 116 | 3 | 10 | 7 |
| Neonatal Invasive | | | | | | | | |
| EOD | 26 | 3 | 1 | 0 | 21 | 0 | 1 | 0 |
| LOD | 35 | 0 | 0 | 0 | 35 | 0 | 0 | 0 |
| Adult invasive | 24 | 4 | 1 | 5 | 10 | 1 | 3 | 0 |
| Carriage | | | | | | | | |
| vagina | 42 | 5 | 7 | 3 | 25 | 0 | 2 | 0 |
| urine | 24 | 5 | 2 | 1 | 14 | 0 | 2 | 0 |
| other | 13 | 0 | 0 | 3 | 8 | 0 | 2 | 0 |
| Animal origin | 13 | 1 | 0 | 0 | 3 | 2 | 0 | 7 |

[a]Reference GBS strains (NEM316, 2603V/R, BM110, COH1 and A909) used as controls are not included in this table.
[b]Abbreviations: EOD, early onset disease; LOD, late onset disease; NT, not typable.

Example 2

Identification and Characterization of Gbs2018 Polymorphism

Extracted DNA was used as a matrix for PCR amplifications. The full-length genes of all allelic forms of gbs2018 were amplified by using primer pair O1-O2 (see table S1 below), respectively located upstream and downstream from the gene.

TABLE S1

Oligonucleotides used in this study.

| Primer | SEQ ID NO | Sequence (5' to 3') | Target | Cluster or Reference |
|---|---|---|---|---|
| O1 | 17 | AAAATAAACGTGG TCCTATCCT | gbs2018 | A, B, C |
| O2 | 18 | GGCAAAGTTCTGA TGAGGTTTG | gbs2018 | A, B, C |

TABLE S1-continued

Oligonucleotides used in this study.

| Primer | SEQ ID NO | Sequence (5' to 3') | Target | Cluster or Reference |
|---|---|---|---|---|
| O3 | 19 | GCAGCGTTTGCTG TATGTAGTGGT | gbs2018 | A, B |
| O4 | 20 | CTTGAGAACGTCT TGACTGC | gbs2018 | A, B |
| O5 | 21 | GGTAAGCAGTCAA GACGTTCTCA | gbs2018 | A, B |
| O6 | 22 | AGTTCCCACAGAG TCTGCAT | gbs2018 | A, B |
| O7 | 23 | AGCACAGGAAGTT GCCCAGAAA | gbs2018 | A, B |
| O8 | 24 | AGCATCACGTAGC TTGTTAG | gbs2018 | A, B, C |
| O9 | 25 | GTTGACCAAGCTT ATGATCATGTGG | gbs2018 | A, B, C |
| O10 | 26 | TTGCTAAGAGTGG ACTTGCG | gbs2018 | A, B, C |
| O11 | 27 | GGCTTCAATGTCA GCGGCGTTTAT | gbs2018-ST-17 | C |
| O12 | 28 | GCTGCATTAAATC CTTCCTGACCA | gbs2018-ST-17 | C |
| O13 | 29 | CCTCATCGTTACA AAGATTCTG | gbs2018-ST-17 | C |
| O14 | 30 | AGCCACCAAGTTT CCGCTAGTA | gbs2018 | A, B, C |
| dltRS | 31 | TTGACAGGTCTCT ATGATTAGTC | dltR | A, B, C |
| dltRAS | 32 | GTCTGGTTCTCAG CCTAATTC | dltR | A, B, C |
| ST-17S | 33 | ATACAAATTCTGC TGACTACCG | gbs2018-ST-17 | C |
| ST-17AS | 34 | TTAAATCCTTCCT GACCATTCC | gbs2018-ST-17 | C |
| Vlac1 | 41 | GAATAACACTTAT TCCTATC | pTCVlac | Poyart and Trieu-Cuot, 1997 |
| Vlac2 | 42 | CTTCCACAGTAGT TCACCACC | pTCVlac | Poyart and Trieu-Cuot, 1997 |

Sau3A-RFLP analysis of the PCR products revealed considerable structural heterogeneity of the gbs2018 locus, which was not simply due to intramolecular rearrangements (deletion/amplification) within the KPEA repeat segment present in NEM316.

To gain insight into the genetic diversity of the gbs2018 alleles, all sixteen PCR fragments were entirely sequenced on both strands with the corresponding PCR primers (see primers O1 to O14 in table S1). The resulting DNA sequences were assembled using "Codoncode Aligner version 1.3.4" software to produce a full length gbs2018 gene. DNA sequences were then analyzed and compared with "DNA Strider version 1.4f3" and "Clustal X version 1.83".

Finally, a phylogenic tree was generated from alignments of gbs2018 sequences using the neighbour-joining method, with "TreeEdit version 1.01a10" software.

As shown in FIG. 6, the resulting phylogenic tree included the gbs2018 gene of sequenced strains NEM316, 2603V/R, and A909. In the latter strain, the gbs2018-like sequence was interrupted by the insertion sequence IS1381. In order to avoid the generation of an aberrant phylogenic tree, the insertion sequence was removed for this analysis and the sequence A909-delta was, hence, reconstructed in silico. Additionally, the star ST-19* denotes one mutation in one of the seven genes analyzed when compared to the reference sequence. DNA sequences assigned to each cluster (A, B, and C), have different characteristics, whereas sequence variations within a given cluster are due mainly to rearrangements within segments containing repeated sequences (see FIG. 6).

The resulting phylogenetic tree revealed the presence of three major clusters designated A, B, and C:
 Cluster A is divided into 4 sublineages and comprises the gbs2018 sequences from strains belonging to ST-19 and ST-23, notably those from the sequenced strains 2603 V/R and NEM316.
 Cluster B includes sequences from strains belonging to 8 different STs (ST-1, ST-2, ST-7, ST-6, ST-8, ST-9, ST-10, and ST-41), among which 3 sublineages were identified.
 Importantly, Cluster C, which contains 2 sublineages, was shown to be exclusively composed of ST-17 sequences. To confirm this observation, the gbs2018 variants from 11 additional ST-17 GBS strains were sequenced, and proved to also belong to cluster C.

The structure of the gbs2018 gene variants was analyzed in detail by using representatives of clusters A (NEM316), B (NEM1010) and C (BM110) as prototype sequences (see FIG. 7). Based on the sequence analysis, the representative members of each phylogenetic clusters A, B, and C, encoding the three allelic forms of the surface protein Gbs2018, were divided into eleven segments, numbered S1 to S11.

Among the eleven segments defined, three were present in all sequences:
 the 5' segment S1, which encodes the signal peptide;
 the 3' segment S8, which encodes the sorting signal made of the "LPXTG" motif followed by a hydrophobic domain and a positively charged tail, and;
 the segment S7, which contains a variable number (n) of repeats encoding a 4-amino-acid long motif based on the sequence "KPEA"; with n ranging between 54 and 126 in clusters A and B, and n=45 in cluster C.

Sequence variations within a given cluster were proved to be mainly due to rearrangements within portions containing repeated sequences. Thus, sequence heterogeneity within cluster A appears to be linked to variations in the number of KPEA repeats in S7 (CCH180, NEM1002) or to a deletion removing the S6 segment. Indeed, segment 6 was surprisingly absent from the gbs2018 genes of the three ST-19 strains (Cluster A) analyzed in this study (2603V/R, NEM940, NEM1560). This deletion is likely due to a recombination event between segments S5 and S7, which share 84% of identity over 36 bp.

In cluster B, the sequence diversity seems to correlate with size variation of segment S7, whereas the two sublineages observed in cluster C are probably due to the number of S11 repeats in gbs2018.

Finally, each cluster was found to contain at least one distinctive segment:

The segment S3 appears to be distinctive of cluster A;

The segment S9, containing 9 repeats encoding a 8-amino-acids long motif based on the sequence "IKAESINT/K", was only found in cluster B;

The segments S10 and S11 seem specific of cluster C. Remarkably, two copies of the segment S11, consisting of the segment S11a followed by the segment S11b, were found in all but two ST-17 strains (COH1 and NEM318) belonging to cluster C.

Example 3

Development of a Real-Time PCR Assay for Specific Detection of GBS Strains and ST17 Variants in Clinical Samples Specific primers dltRS and dltRAS were designed to detect GBS strains by PCR. Indeed, this couple of primers allows the amplification of a 234-bp fragment in presence of dltR, a monocopy regulator gene specifically encountered in *S. agalactiae* [Poyart C. et al., 2001].

Based on the polymorphism of gbs2018 observed in the above-mentioned example 2, the sequence of the C cluster-specific S10 domain was used to design ST-17 specific primers ST-17A and ST-17AS, which would generate a 210-bp amplicon fragment from the gbs2018 specific segment S10.

In both cases, optimized primer sequences were designed with "Beacon Designer 4.01" and their sequences were compared against the Genbank database using BLAST searches to verify the absence of serendipitous similarities.

The real-time PCR assays enabling the detection of GBS strains and ST-17 variants from isolated colonies or from clinical samples using primer pairs ST-17A/ST-17AS and dltRS/dltRAS were conducted in separate reactions.

PCR assays were performed on a LightCycler® 2.0 Instrument (Roche Molecular Diagnostics) in a final volume of 25 µl containing 5 µl of extracted DNA or distilled H2O (for the negative control), 0.45 mM each of sense and antisense primers, 2 µl of 10× LightCycler-DNA Master SYBR Green I (Roche Molecular Biochemicals, Mannheim, Germany), and 4.0 mM MgCl2.

The PCR mixtures were subjected to a precycle of 95° C. for 10 min. The amplification was performed using 40 cycles of 95° C. for 10 sec, 5 sec at 55° C. and 72° C. for 10 sec. At the end of 40 amplification cycles, the reaction was heated to 95° C. and then cooled to 35° C. The reaction product was then subjected to a post-PCR melting cycle or was analyzed by agarose gel electrophoresis.

The melting profile was performed using software programs provided in the LightCycler instrument (Version 4.0). In the LightCycler, a positive result for an ST-17 GBS strain gave two curves with melting temperatures (Tm) of 79.5+0.4 (dltR) and 78.5+0.3 (ST-17) respectively, while a non ST-17 GBS strain gave only one melting curve with a Tm of 79.5+0.4.

Positive and negative controls were included in all runs:

DNA extracted from the reference strain *S. agalactiae* BM110 was used as positive control; analytical sensitivity of the method was assessed by serial tenfold dilutions of BM110 genomic DNA. The calibrator/positive controls were two dilutions corresponding to $10^3$ and $10^1$ GBS bacterial genomes.

As negative control, water was added instead of DNA.

The absence of inhibitors in all negative PCR samples was checked by using an internal control, in which plasmid DNA was added at a final concentration of 10 copies per PCR reaction which allowed amplification of a 125-bp DNA fragment in the presence of specific primers Vlac1 and Vlac2 (see table S1 above).

Moreover, strict precautions were taken to prevent cross-contamination: thus, procedures performed before and after PCR manipulations were conducted in separate rooms.

The specificity of the PCR assays was also verified using DNA extracted from pure cultures of a variety of Gram-positive and Gram-negative bacterial species from the inventors' laboratory collection. These included numerous streptococci and other microorganisms of the normal intestinal and genital flora, as well as bacteria that cause genital tract infections, as it can be seen in the Table S2 below.

TABLE S2

Bacterial strain panels used to test specificity of the real-time PCR assay.

| Organism | Source | Organism | Source |
|---|---|---|---|
| Gram-positive panel | | | |
| Streptococcus agalactiae | CIP 103227 T | Staphylococcus aureus | CIP 65.8 T |
| Streptococcus anginosus | CIP 102921 T | Staphylococcus auricularis | CIP 103587 T |
| Streptococcus bovis | CIP 102302 T | Staphylococcus capitis | CIP 81.53 T |
| Streptococcus canis | CIP 103223 T | Staphylococcus cohnii | CIP 81.54 T |
| Streptococcus constellatus | CIP 103247 T | Staphylococcus epidermidis | CIP 81.55 T |
| Streptococcus cricetus | CIP 102510 T | Staphylococcus haemolyticus | CIP 81.56 T |
| Streptococcus downei | CIP 103222 T | Staphylococcus hominis | CIP 81.57 T |
| Streptococcus dysgalactiae | CIP 102914 T | Staphylococcus hyicus | CIP 81.58 T |
| Streptococcus equinus | CIP 102504 T | Staphylococcus intermedius | CIP 81.60 T |
| Streptococcus dysgalactiae | CIP 102914 | Staphylococcus lugdunensis | CIP 103642 T |
| Streptococcus equi subsp. zooepidemicus | CIP 103228 T | Staphylococcus saprophyticus | CIP 76.125 T |
| Streptococcus gallolyticus | CIP 105428 T | Staphylococcus schleiferi | CIP 104370 T |
| Streptococcus gordonii | CIP 105258 T | Staphylococcus sciuri | CIP 105826 T |
| Streptococcus intermedius | CIP 102508 T | Staphylococcus warneri | CIP 81.65 T |
| Streptococcus infantarius | | Staphylococcus xylosus | CIP 81.66 T |
| Streptococcus lutetiensis | CIP106849 T | Lactococcus lactis | MG1363 |
| Streptococcus mitis | CIP 103335 T | Lactococcus garvieae | CIP 102507 T |
| Streptococcus mutans | CIP 103694 | Abiotrophia defectiva | NE1418 |
| Streptococcus oralis | CIP 10922 T | Granulicatella adiacens | CIP 103243 T |
| Streptococcus parasanguinis | CIP 104372 T | Listeria monocytogenes | L028 |

TABLE S2-continued

Bacterial strain panels used to test specificity of the real-time PCR assay.

| Organism | Source | Organism | Source |
|---|---|---|---|
| *Streptococcus parauberis* | CIP 103956 T | *Bacillus subtilis* | W163 |
| *Streptococcus pasteurianus* | CIP 107122 T | *Bacillus cereus* | CCH collection |
| *Streptococcus pneumoniae* | CIP 102911 T | *Bifidobacterium breviae* | CCH collection |
| *Streptococcus porcinus* | CIP 103218 T | *Corynebacterium pseudogenitalium* | CCH collection |
| *Streptococcus pyogenes* | CIP 56.41 T | *Corynebacterium urealyticum* | CCH collection |
| *Streptococcus salivarius* | CIP 102509 T | *Lactobacillus casei* | CCH collection |
| *Streptococcus sanguinis* | CIP 55.1328T | *Clostridium difficile* | CCH collection |
| *Streptococcus sobrinus* | CIP 103230 T | *Clostridium perfringens* | CCH collection |
| *Streptococcus suis* | CIP 103217 T | *Peptostreptococcus anaerobius* | CCH collection |
| *Streptococcus thermophilus* | CIP 102303 T | *Peptostreptococcus magnus* | CCH collection |
| *Streptococcus uberis* | CIP 103219 T | *Peptostreptococcus prevotii* | CCH collection |
| *Streptococcus vestibularis* | CIP 103363 T | *Propionibacterium acnes* | CCH collection |
| *Enterococcus avium* | CIP 103019 T | *Facklamia hominis* | CIP 105962 T |
| *Enterococcus casseliflavus* | CIP 103018 T | *Enterococcus faecium* | CIP 103014 T |
| *Enterococcus durans* | CIP 55.125 T | *Leuconostoc mesenteroides* | CIP 102388 |
| *Enterococcus faecalis* | CIP 103015 T | *Pediococcus acidilactici* | CIP 101954 |
| *Enterococcus gallinarum* | CIP 103013 T | *Stomatococcus mucilaginosus* | CCH collection |
| *Enterococcus hirae* | CIP 53.48 T | *Aerococcus urinae* | CCH collection |
| *Enterococcus raffinosus* | CIP103329 T | | |
| *Enterococcus solitarius* | | | |
| Gram-negative panel | | | |
| *Acinetobacter baumannii* | CCH collection | *Klebsiella pneumoniae* | CCH collection |
| *Achromobacter xyloxoxidans* | CCH collection | *Legionella pneumophila* | CCH collection |
| *Actinobacillus ureae* | CCH collection | *Moraxella osloensis* | CCH collection |
| *Aeromonas hydrophila* | CCH collection | *Moraxella canis* | CCH collection |
| *Bacteroides fragilis* | CCH collection | *Morganella morganii* | CCH collection |
| *Brucella melitensis* | CCH collection | *Neisseria gonorrhoeae* | CCH collection |
| *Bulkholderia cepacia* | CCH collection | *Neisseria menigitidis* | CCH collection |
| *Campylobacter fetus* | CCH collection | *Neisseria mucosa* | CCH collection |
| *Campylobacter coli* | CCH collection | *Pasteurella multocida* | CCH collection |
| *Cardiobacterium hominis* | CCH collection | *Porphyromonas gingivalis* | CCH collection |
| *Citrobacter diversus* | CCH collection | *Proteus mirabilis* | CCH collection |
| *Citrobacter freundii* | CCH collection | *Proteus vulgaris* | CCH collection |
| *Eikenella corrodens* | CCH collection | *Providencia stuartii* | CCH collection |
| *Enterobacter aerogenes* | CCH collection | *Pseudomonas aeruginosa* | CCH collection |
| *Enterobacter cloacae* | CCH collection | *Pseudomonas fluorescens* | CCH collection |
| *Escherichia coli* | CCH collection | *Pseudomonas stutzeri* | CCH collection |
| *Gardnerella vaginalis* | CCH collection | *Salmonella typhimurium* | CCH collection |
| *Haemophilus influenzae* | CCH collection | *Serratia marcescens* | CCH collection |
| *Haemophilus parainfluenzae* | CCH collection | *Shigella sonnei* | CCH collection |
| *Hafnia alvei* | CCH collection | *Stenotrophomonas maltophilia* | CCH collection |
| *Kingella kingae* | CCH collection | *Yersinia enterocolitica* | CCH collection |
| *Klebsiella oxytoca* | CCH collection | *Mycoplasma hominis* | CCH collection |

Figure 8:
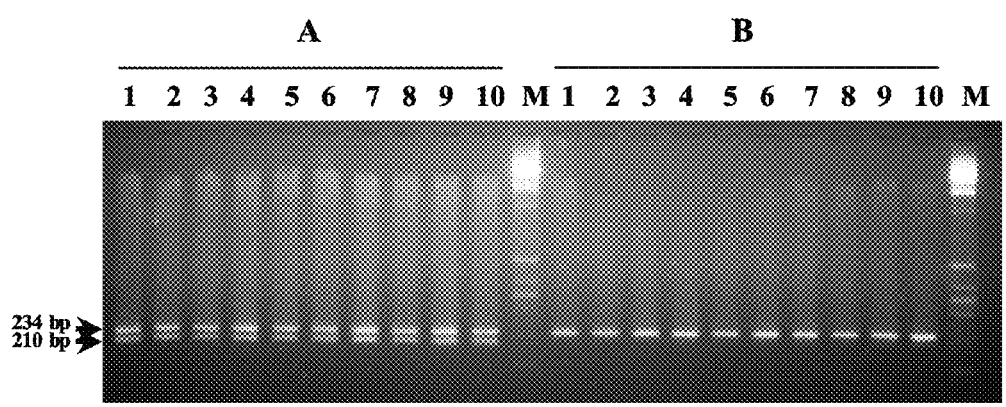

Finally, a bacterial collection of 181 GBS strains was thus characterized by PCR using both primer pairs dltRS/dltRAS and ST-17S/ST-17AS in the same reaction. In this analysis, 8 invasive clones previously identified as ST-17 strains were present as positive controls and the sequenced strains NEM316 (ST-23) and 2603V/R (ST-19*) were used as negative controls. As expected, primers dltRS/dltRAS yielded the expected PCR fragments with all 181 GBS strains studied whereas primers ST-17A and ST-17AS gave a positive reaction with 50 clinical human isolates. An example of the amplification pattern obtained with the two couples of primers is shown in FIG. 8.

All strains that were screened as PCR-positive with ST-17 primers were also shown to belong to serotype III and all but one revealed to be isolated from human invasive infections (see Table 2 below). In order to evaluate the results obtained by amplification, MLST was carried out for 42 strains and all were confirmed as ST-17 (Table 2). Similarly, MLST was performed on 61 of the remaining 131 ST-17 PCR-negative strains, of which 19 neonatal invasive strains (11 strains from EOD, 7 strains from LOD, and one strain isolated from a 3-year-old child), 19 adult invasive strains, 11 carriage strains, and 12 strains from bovine mastitis, confirmed that none of these belonged to ST-17.

TABLE 2

Characteristics of human GBS isolates according to ST and specific ST-17A/ST-17AS PCR assay.

| ST | No of isolates in ST | PCR+ ST-17A/ ST-17AS | Serotypes (no of isolates) | Origin (no. of isolates) |
|---|---|---|---|---|
| 1 | 7 | 0 | III (2), V (5) | C (3), AI (4) |
| 2 | 3 | 0 | III (2), II (1) | EOD (1), LOD (1), AI (1) |
| 6 | 1 | 0 | Ib (1) | EOD (1) |
| 8 | 5 | 0 | Ia (3), Ib (2) | EOD (1), C (2), AI (2) |
| 9 | 1 | 0 | II (1) | AI (1) |
| 10 | 6 | 0 | Ib (2), II (3), IV (1) | C (3), AI (3) |
| 12 | 1 | 0 | Ib | C(1) |
| 17 | 50 | 50 | III (50) | EOD (15), LOD (28), C (1), AI (4), NI (2) [b] |
| 19 | 11 | 0 | Ia (1), II, (2), III (6), V (1), NT (1) | EOD (1), LOD (2), AI (7), HI (1) [c] |

TABLE 2-continued

Characteristics of human GBS isolates according to ST and specific ST-17A/ST-17AS PCR assay.

| ST | No of isolates in ST | PCR+ ST-17A/ ST-17AS | Serotypes (no of isolates) | Origin (no. of isolates) |
|---|---|---|---|---|
| 23 | 12 | 0 | III (5), Ia (4), Ib (3) | EOD (4), LOD (3), AI (2), C (2), NI (1)[d] |
| 41 | 1 | 0 | III (1) | LOD (1) |

Abbreviations: ST, sequence type ; C, carriage strain ; EOD, early onset disease ; LOD, late onset disease ; NI, neonatal invasive; AI, adult invasive strain; HI, human invasive strain;
[b] GBS BM110 and GBS COHI;
[c] GBS 2603V/R;
[d] GBS NEM316

As it is shown in table 2, the most frequent ST found among human strains was ST-23 (14 strains) followed by ST-19 (10 strains), ST-1 (6 strains), ST-8 (5 strains), ST-10 (6 strains), and ST-2 (3 strains); all other STs were represented by one strain.

Finally, 85 vaginal samples from pregnant women collected over a 1 month period (December 2004) were comparatively analyzed using the conventional direct plate culture method for GBS detection and the real-time PCR assay of the present invention:

The plate culture method identified 13 (15.2%) GBS-positive cultures after 24 h at 37° C. Serotype distribution (number of strain) was as follows: III (5), Ia (2), and Ib (6).

The real-time PCR assay performed on DNA extracted directly from the vaginal samples confirmed the presence of GBS in the 13 samples, and that of a ST-17 strain in 2 samples. These results were further confirmed by MLST. Moreover, the PCR assay was negative for the 72 remaining samples, and the absence of inhibitors was assessed using the internal PCR plasmid DNA control which gave a positive signal in all cases.

Thus, we developed a real-time PCR assay enabling rapid, simple, reliable, and accurate detection of the "highly-virulent" GBS ST-17 lineage on bacterial cultures or directly on vaginal secretions. Using this technique, accurate identification of women and neonates colonised by ST-17 can be readily achieved within less than two hours.

Example 4

Group B *Streptococcus* Epidemiology Report 58 strains from different geographical French areas and responsible for invasive infections were studied: 28 unrelated neonatal invasive strains and 30 non-redundant strains isolated from adult invasive infections. All strains received were further characterized as indicated: confirmation of the assigned identification and characterization of the antibiotic susceptibility, determination of the capsular serotype by PCR-based molecular serotyping (Poyart et al., 2006), and detection of the hypervirulent ST-17 clone by real-time PCR (as described above and in Lamy et al., 2006).

I. Neonatal Invasive Infections

Among the 58 isolates studied, 28 non-redundant strains were isolated from neonatal invasive diseases and 16 and 12 out of these strains were from early onset disease (EOD; i.e., disease occurring up to 6 days after birth) and from late onset disease (LOD, i.e., disease occurring from 7 days to 3 months of age), respectively (see Table 3).

EOD strains:

Ten (62.5%) out of the 16 EOD strains were isolated from blood cultures, 2 of them are isolated from blood cultures and cerebrospinal fluids, and the remaining 6 strains were from gastric samples of neonates with neonatal infection symptoms (breathing difficulty, shock, and pneumonia). Molecular capsular serotyping revealed that the 16 EOD isolates belonged to serotype III (n=8; 50%), Ia (n=6; 37.5%), II (n=1; 6.25%), or V (n=1; 6.25%). The 10 strains isolated from blood cultures were of serotype Ia (n=5, 50%), III (n=4, 40%), and V (n=1, 10%). Among these strains, the two strains responsible for meningitis were of serotype Ia and III. The 6 strains from gastric fluids belonged to serotypes III (n=4, 66.6%) and Ia (n=2; 33.3%). The PCR-detection of the ST-17 hypervirulent clone was positive for the 8 serotype III EOD strains which included 5 blood isolates, including one isolate responsible for meningitis, and 3 isolates from gastric fluids.

LOD Strains:

All 12 LOD strains were isolated from blood culture, belonged to serotype III, and were identified as CT-17 clone. Nine out of these 12 isolates (75%) were also recovered from CSF and were responsible for meningitis.

TABLE 3

Characteristics of the GBS neonatal invasive strains

| Capsular serotype | Neonatal invasive infection | | |
|---|---|---|---|
| | EOD (%)[a] | LOD (%)[b] | Total |
| Ia | 6 (37.5) | 0 | 6 (21.4) |
| Ib | 0 | 0 | 0 |
| II | 1 (6.25) | 0 | 1 (3.6) |
| III | 8 (50) | 12 (100) | 20 (71.4) |
| IV | 0 | 0 | 0 |
| V | 1 (6.25) | 0 | 1 (3.6) |
| VI, VII, VIII | 0 | 0 | 0 |
| Total | 16 (60.7) | 12 (39.3) | 28 (100) |
| ST-17clone | 8 (50) | 12 (100) | 20 (71.4) |

[a] EOD (early onset disease); 10 (62.5%) strains were isolated from blood cultures, 2 of them (12.5%) were from blood cultures and cerebrospinal fluid (CSF), and 6 (37.5%) strains were from gastric samples.
[b] LOD (late onset disease); All strains (n = 12) were isolated from blood cultures and among these 8 (72.7%) were also isolated in CSF and were responsible for meningitis.

These results demonstrate that the association between strain invasiveness and ST-17 lineage in neonates with LOD is highly significant (p<0.0001) as all 12 invasive strains studies were ST-17. In EOD, the ST-17 clonal complex accounted for 8 out of the 16 strains studied (50%) (p<0.01) although it corresponded to 100% of the serotype III strains (n=8). This confirms that a majority of GBS isolates responsible for neonatal invasive infections in France are ST-17. Similar results have also been reported in other countries (Bisharat et al, 2004; Bohnsack et al, 2004; Jones et al, 2006; Lin et al, 2006).

II. Adult Invasive Infections 30 non-redundant strains were isolated from adult invasive infections, sepsis and arthritis being the two main clinical symptomatologies.

The characteristics of these strains are listed in Table 4.

TABLE 4

Characteristics of GBS adult invasive infections.

| Capsular serotype | Number of strains (%) | Adult invasive infection Clinical symptomatology |
|---|---|---|
| Ia | 8 (26.6) | Bacteraemia (4), arthritis (2), meningitis (1), matenofetal infection (1) |
| Ib | 1 (3.3) | Bacteraemia (1) |
| II | 3 (10) | Bacteraemia (3) |
| III | 10 (33.3) | Bacteraemia (2), arthritis (5), meningitis (2), maternofetal infection (1) |
| IV | 0 | |
| V | 8 (26.6) | Bacteraemia (5), arthritis (2), endometritis (1) |
| VI, VII, VIII | 0 | |
| Total | 30 (100) | Bacteraemia (15), arthritis (9), meningitis (3), maternofetal infection (2), endometritis (1) |
| ST-17 clone | 2 (6.6) | Arthritis (1), maternofetal infection (1) |

The most prevalent capsular serotypes were III (33.3%), Ia (26.6%), and V (26.6%). Fifteen (50%) out of the 30 strains were isolated from blood cultures and nine (30%) were responsible for arthritis and isolated from an articular punction. No predominance of a capsular serotype was noticed among the strains responsible for bacteraemia and arthritis. Three out of the 30 strains studied were responsible for meningitis (2 serotype III and 1 serotype Ia strains). Among the 10 serotype III isolates of this collection, only two were identified as ST-17 (20%) but none of them was responsible for meningitis.

These results demonstrate that the epidemiology of GBS strains responsible for invasive infection in adults differs drastically from that observed in neonates.

III. Prevalence of the Hypervirulent ST-17 Clone Among Serotype III GBS Isolated from Vaginal Samples In order to study the prevalence of the hypervirulent ST-17 clone among GBS colonizing vagina of pregnant women, all GBS stains isolated from vaginal samples collected from pregnant women at the Cochin hospital during a one-year period (from Jan. 6, 2005 to Jan. 6, 2006) were studied. All serotype III GBS detected by agglutination method were confirmed by molecular serotyping. PCR detection of the ST-17 clone was carried out for all serotype III strains whose serotyping was confirmed by molecular technique. The results obtained are shown in table 5.

A total of 3235 non-redundant vaginal samples were analyzed, 325 were positive for GBS and, among these, 113 strains were of serotype III (35%). Forty-seven (41.6%) out of the 113 serotype III strains were ST-17. In conclusion, GBS carriage was detected in 10% of the pregnant women studied and a serotype III strain was present in 34.76% of the colonized women. The percentage of ST-17 clone in this serotype III GBS population was 41.6%.

TABLE 5

Prevalence of the hypervirulent ST-17 clone among serotype III GBS isolated from vaginal samples of pregnant women.

| | Vaginal samples[a] |
|---|---|
| Total | 3235 |
| GBS positive | 325 (10%) |
| Serotype III GBS | 113 (3.5%, 34.8%) |
| ST-17clone | 47 (1.5%, 14.5%) |

[a]The first and second percentage are calculated relative to the number of vaginal samples (n = 3235) or to the number of vaginal samples positive with GBS (n = 325).

It is worth noting that the epidemiological characteristics (serotype and ST-17 prevalence) of the GBS strains in pregnant women and in EOD are almost identical (see Table 3 and Table 5). This observation gives further support to our proposal that detection of the hyper-virulent clone ST-17 in vaginal sample should be carried out in order to ensure accurate follow up of babies colonized by this clone.

REFERENCES

Bisharat, N., Crook, D. W., Leigh, 1, Harding, R M., Ward, P. N., Coffey, T. J., Maiden, M. C., Peto, T., and Jones, N. (2004) Hyperinvasive neonatal group B *streptococcus* has arisen from a bovine ancestor. *J Clin Microbiol* 42: 2161-2167.

Bohnsack, J. F., Whiting, A. A., Martinez, G., Jones, N., Adderson, E. E., Detrick, S., Blaschke-Bonkowsky, A. J., Bisharat, N., and Gottschalk, M. (2004) Serotype III *Streptococcus agalactiae* from bovine milk and human neonatal infections. *Emerg Infect Dis* 10: 1412-1419.

Gaillot O, Poyart C, Berche P and Trieu-Cuot P. Molecular characterization and expression analysis of the superoxide dismutase gene from *Streptococcus agalactiae*. Gene 1997 Dec. 19; 204:213-8.

Holland P M, Abramson R D, Watson R, Gelfand D H. Detection of specific polymerase chain reaction product by utilizing the 5'----3' exonuclease activity of *Thermus aquaticus* DNA polymerase. Proc Natl Acad Sci USA. 1991 Aug. 15; 88(16):7276-80.

Huang Q, Fu W L. Comparative analysis of the DNA staining efficiencies of different fluorescent dyes in preparative agarose gel electrophoresis. Clin Chem Lab Med 2005; 43(8):841-2.

Jones N, Bohnsack J F, Takahashi S, et al. Multilocus sequence typing system for group B *streptococcus*. J Clin Microbiol 2003; 41:2530-6.

Jones, N., Oliver, K. A., Barry, J., Harding, R. M., Bisharat, N., Spratt, B. G., Peto, T., and Crook, D. W. (2006) Enhanced invasiveness of bovine-derived neonatal sequence type 17 group B *streptococcus* is independent of capsular serotype. *Clin Infect Dis* 42: 915-924.

Lamy, M. C., Dramsi, S., Billoet, A., Reglier-Poupet, H., Tazi, A., Raymond, J., Guerin, F., Couve, E., Kunst, F., Glaser, P., Trieu-Cuot, P., and Poyart, C. (2006) Rapid detection of the "highly virulent" group B *streptococcus* ST-17 clone. *Microbes Infect* 8: 1714-1722.

Lin, F. Y., Whiting, A., Adderson, E., Takahashi, S., Dunn, D. M., Weiss, R., Azimi, P. H., Philips, J. B., 3rd, Weisman, L. E., Regan, J., Clark, P., Rhoads, G. G., Frasch, C E., Troendle, J., Moyer, P., and Bolinsack, J. F. (2006) Phylogenetic lineages of invasive and colonizing strains of serotype III group B St-eptococci from neonates: a multicenter prospective study./*Clin Microbiol* 44: 1257-1261.

Luan S L, Granlund M, Sellin M, Lagergard T, Spratt B G, Norgren M. Multilocus sequence typing of Swedish invasive group B *streptococcus* isolates indicates a neonatally associated genetic lineage and capsule switching. J Clin Microbiol 2005; 43:3727-33.

Musser, J. M., S. J. Mattingly, R. Quentin, A. Goudeau, and R. K. Selander. Identification of a high-virulence clone of type III *Streptococcus agalactiae* (group B *streptococcus*) causing invasive neonatal disease. Proc. Natl. Acad. Sci. USA 1989; 86:4731-4735

Poyart C, Lamy M C, Boumaila C, Fiedler F and Trieu-Cuot P. Regulation of D-alanyl-lipoteichoic acid biosynthesis in *Streptococcus agalactiae* involves a novel two-component regulatory system. J Bacteriol 2001; 183:6324-34.

Poyart, C, Billoet, A., Tavares, N., Raymond, J., Tazi, A., and Trieu-Cuot, P. (2006) A Multiplex PCR Assay For Rapid Identification of the Nine Capsular Serotypes of *Streptococcus agalactiae*. *J Clin Microbiol* (submitted).

Reglier-Poupet H, Quesne G, Le Theo E et al. Prospective evaluation of a real-time PCR assay for detection of group B streptococci in vaginal swabs from pregnant women. Eur J Clin Microbiol Infect Dis 2005; 24:355-7

Schrag, S. (2004) The past and the future of perinatal group B streptococcal disease prevention. *Clin Infect Dis* 39: 1136-1138.

Schrag, S. J., Zell, E. R., Lynfield, R., Roome, A., Arnold, K. E., Craig, A. S., Harrison, L. H., Reingold, A., Stefonek, K., Smith, G., Gamble, M., and Schuchat, A. (2002) A population-based comparison of strategies to prevent early-onset group B streptococcal disease in neonates. *N Engl J Med* 347: 233-239.

Schuchat, A. (1999) Group B *streptococcus*. Lancet 353: 51-56.

Stålhammar-Carlemalm, M., L. Stenberg, and G. Lindahl. Protein Rib: a novel group B streptococcal cell surface protein that confers protective immunity and is expressed by most strains causing invasive infections. J Exp Med 1993; 177:1593-1603

Tettelin H et al. Genome analysis of multiple pathogenic isolates of *Strpetococcus agalactiae*: implications for the microbial "pan-genome". Proc Nat Acad Sci 2005; 102: 13950-55.

Tyagi S, Kramer F R. Molecular beacons: probes that fluoresce upon hybridization. Nat Biotechnol. 1996 March; 14(3):303-8.

Wessels M R, Haft R F, Heggen L M, Rubens C E. Identification of a genetic locus essential for capsule sialylation in type III group B streptococci. Infect Immun. 1992 February; 60(2):392-400

Whitcombe D, Theaker J, Guy S P, Brown T, Little S. Detection of PCR products using self-probing amplicons and fluorescence. Nat Biotechnol 1999; 17(8):804-7.

Wittwer C T, Ririe K M, Andrew R V, et al. The LightCycler: a microvolume multisample fluorimeter with rapid temperature control. Biotechniques 1997; 22:176-81.

---

The invention claimed is:

1. A method for the in vitro detection of a high-virulence group B *streptococcus* strain of the ST-17 clone comprising:

providing a biological sample comprising nucleic acid;

hybridizing the nucleic acid of the biological sample with a nucleic acid molecule that hybridizes to a nucleotide sequence consisting of the S10 nucleotide sequence of SEQ ID NO:5, the S11a nucleotide sequence of SEQ ID NO: 13, or the S11b nucleotide sequence of SEQ ID NO: 15, or the complements thereof; and detecting the presence or absence of the ST-17 clone by detecting the presence or absence of the S10, S11a or S11b nucleotide sequence or the complement thereof in the nucleic acid of the biological sample.

2. The method of claim 1, further comprising hybridizing a positive control to the nucleic acid molecule that hybridizes to a nucleotide sequence consisting of the S10 nucleotide sequence of SEQ ID NO: 5, the S11a nucleotide sequence of SEQ ID NO: 13 or the S11b nucleotide sequence of SEQ ID NO: 15, or the complements thereof.

3. The method of claim 2, further comprising hybridizing a negative control to the nucleic acid molecule that hybridizes to a nucleotide sequence consisting of the S10 nucleotide sequence of SEQ ID NO: 5, the S11a nucleotide sequence of SEQ ID NO: 13 or the S11b nucleotide sequence of SEQ ID NO: 15, or the complements thereof.

4. The method of claim 1, further comprising hybridizing a negative control to the nucleic acid molecule that hybridizes to a nucleotide sequence consisting of the S10 nucleotide sequence of SEQ ID NO: 5, the S11a nucleotide sequence of SEQ ID NO: 13 or the S11b nucleotide sequence of SEQ ID NO: 15, or the complements thereof.

5. The method of claim 1, comprising hybridizing the nucleic acid of the biological sample with a nucleic acid molecule that hybridizes to a nucleotide sequence consisting of the S10 nucleotide sequence of SEQ ID NO: 5, or the complement thereof.

6. The method of claim 5, further comprising amplifying the nucleic acid of the biological sample using a polymerase chain reaction.

7. The method of claim 5, wherein the nucleic acid molecule that hybridizes to a nucleotide sequence consisting of the nucleotide sequence of SEQ ID NO:5, or the complement thereof, is a primer consisting of the nucleotide sequence of SEQ ID NO:33 or SEQ ID NO:34.

8. The method of claim 1, comprising hybridizing the nucleic acid of the biological sample with a nucleic acid molecule that hybridizes to a nucleotide sequence consisting of the S11a nucleotide sequence of SEQ ID NO: 13, or the complement thereof.

9. The method of claim 8, further comprising amplifying the nucleic acid of the biological sample using a polymerase chain reaction.

10. The method of claim 1, comprising hybridizing the nucleic acid of the biological sample with a nucleic acid molecule that hybridizes to a nucleotide sequence consisting of the S11b nucleotide sequence of SEQ ID NO. 15, or the complement thereof.

11. The method of claim 10, further comprising amplifying the nucleic acid of the biological sample using a polymerase chain reaction.

12. A method for the in vitro detection of a high-virulence group B *streptococcus* strain of the ST-17 clone comprising:
providing a biological sample comprising nucleic acid;
amplifying a fragment of a segment S10 nucleotide sequence or a fragment of a segment S11a or segment S11b nucleotide sequence of the ST-17 clone in the nucleic acid of the biological sample with primers that amplify a fragment of the segment S10 nucleotide sequence of SEQ ID NO: 5, the segment S11a nucleotide sequence of SEQ ID NO: 13 or the segment S11b nucleotide sequence of SEQ ID NO: 15; and
detecting the ST-17 clone by detecting the S10, S11a or S11b amplification product.

13. The method of claim 12, comprising amplifying a nucleic acid sequence within the segment S10 nucleic acid sequence, wherein the primers amplify a fragment of a nucleotide sequence consisting of the nucleotide sequence of SEQ ID NO:5.

14. The method of claim 13, wherein the amplifying comprises a polymerase chain reaction (PCR).

15. The method of claim 13, wherein at least one of the primers is selected from the group of primers consisting of the nucleotide sequences of SEQ ID NO:33; SEQ ID NO:34; SEQ ID NO:28; SEQ ID NO:27; and SEQ ID NO:29.

16. The method of claim 13, wherein two of the primers are selected from the group primers consisting of the nucleotide sequences of SEQ ID NO:33; SEQ ID NO:34; SEQ ID NO:28; SEQ ID NO:27; and SEQ ID NO:29.

17. The method of claim 16, wherein two of the primers are selected from the group primers consisting of the nucleotide sequences of SEQ ID NO:33 and SEQ ID NO:34.

18. The method of claim 12, comprising amplifying a nucleic acid sequence within the segment S11a nucleic acid sequence, wherein the primers amplify a fragment of a nucleotide sequence consisting of the segment S11a nucleotide sequence of SEQ ID NO:13.

19. The method of claim 18, wherein the amplifying comprises a polymerase chain reaction (PCR).

20. The method of claim 12, comprising amplifying a nucleic acid sequence within the segment S11b nucleic acid sequence, wherein the primers amplify a fragment of a nucleotide sequence consisting of the segment S11b nucleotide sequence of SEQ ID NO:15.

21. The method of claim 20, wherein the amplifying comprises a polymerase chain reaction (PCR).

22. The method of claim 12, wherein the amplifying comprises a polymerase chain reaction (PCR).

23. A method for the in vitro detection of a high-virulence group B *streptococcus* strain of the ST-17 clone comprising:
providing a biological sample comprising nucleic acid;
adding to the biological sample a primer set that amplifies a fragment of the S10 nucleotide sequence of SEQ ID NO:5;
subjecting the biological sample to an amplification reaction; and
detecting the presence or absence of the ST-17 clone by detecting the presence or absence of an amplification product of the S10 nucleotide sequence in the nucleic acid of the biological sample.

24. The method of claim 23, wherein the amplification reaction is a polymerase chain reaction.

25. The method of claim 23, wherein primer set has the nucleotide sequences of SEQ ID NO:33 and SEQ ID NO:34.

26. A method for the in vitro detection of a high-virulence group B *streptococcus* strain of the ST-17 clone comprising:
providing a biological sample comprising nucleic acid;
adding to the biological sample a primer set that amplifies a fragment of the segment S10 nucleotide sequence of SEQ ID NO: 5, the segment S11a nucleotide sequence of SEQ ID NO: 13 or the segment S11b nucleotide sequence of SEQ ID NO: 15;
subjecting the biological sample to an amplification reaction; and
detecting the presence or absence of the ST-17 clone by detecting the presence or absence of an amplification product of the segment S10, segment S11a or segment S11b nucleotide sequence in the nucleic acid of the biological sample.

* * * * *

SEQUENCE LISTING

```
<160> NUMBER OF SEQ ID NOS: 48

<210> SEQ ID NO 1
<211> LENGTH: 1569
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1566)

<400> SEQUENCE: 1 atg aat aat aac gaa aaa aaa gta aaa tac ttt tta aga aaa aca gct        48
Met Asn Asn Asn Glu Lys Lys Val Lys Tyr Phe Leu Arg Lys Thr Ala
1               5                   10                  15 tat ggt ttg gct tca atg tca gcg gcg ttt ata gta tgt agt ggt att        96
Tyr Gly Leu Ala Ser Met Ser Ala Ala Phe Ile Val Cys Ser Gly Ile
            20                  25                  30 gta aat act cct aca gtg tct gct gat agt cct gat aca tta aaa gtc       144
Val Asn Thr Pro Thr Val Ser Ala Asp Ser Pro Asp Thr Leu Lys Val
        35                  40                  45 gaa aaa tta ggc aaa ttg aaa gat gtg aaa tca gtt cat gaa ctc aca       192
Glu Lys Leu Gly Lys Leu Lys Asp Val Lys Ser Val His Glu Leu Thr
    50                  55                  60 ccc ata tca ata ccg aac gaa tta aaa ggt gct aaa gag caa gca ctt       240
Pro Ile Ser Ile Pro Asn Glu Leu Lys Gly Ala Lys Glu Gln Ala Leu
65                  70                  75                  80 tct tca ata att tca cat cct aat ata act aat tcg gaa gta gac aaa       288
Ser Ser Ile Ile Ser His Pro Asn Ile Thr Asn Ser Glu Val Asp Lys
                85                  90                  95 cta gct agt gac tat agt ttt aga att aat aca tct aat gat gtg aac       336
Leu Ala Ser Asp Tyr Ser Phe Arg Ile Asn Thr Ser Asn Asp Val Asn
            100                 105                 110 gac gtt aaa cgt cta tta aat gaa ttt tat aac gca gtt gca agg aaa       384
Asp Val Lys Arg Leu Leu Asn Glu Phe Tyr Asn Ala Val Ala Arg Lys
        115                 120                 125 cag tta gat aca aat tct gct gac tac cgt agt aaa att gat aat atc       432
Gln Leu Asp Thr Asn Ser Ala Asp Tyr Arg Ser Lys Ile Asp Asn Ile
    130                 135                 140
```

```
agt act aca ggt ctt gcg ata gct ctt gag gct aaa gaa att tat gaa    480
Ser Thr Thr Gly Leu Ala Ile Ala Leu Glu Ala Lys Glu Ile Tyr Glu
145                 150                 155                 160 gca aat aaa tct ata tta cct cat cgt tac aaa gat tct gtt gga act    528
Ala Asn Lys Ser Ile Leu Pro His Arg Tyr Lys Asp Ser Val Gly Thr
                165                 170                 175 tat gtg aac agt ttt gag gaa aga cga agt cca gga aaa ttt aat att    576
Tyr Val Asn Ser Phe Glu Glu Arg Arg Ser Pro Gly Lys Phe Asn Ile
            180                 185                 190 tgg aat ggt cag gaa gga ttt aat gca gct caa aaa ttg tta gaa gat    624
Trp Asn Gly Gln Glu Gly Phe Asn Ala Ala Gln Lys Leu Leu Glu Asp
        195                 200                 205 gtt aaa aaa tta tta ctt gag cta caa aat tta aca aaa aat aac aaa    672
Val Lys Lys Leu Leu Leu Glu Leu Gln Asn Leu Thr Lys Asn Asn Lys
    210                 215                 220 cca aat att caa gta cct aaa caa gca cct aca gaa gct gca aaa cca    720
Pro Asn Ile Gln Val Pro Lys Gln Ala Pro Thr Glu Ala Ala Lys Pro
225                 230                 235                 240 gct ttg tca cca gaa gcc ttg aca aga ttg act aca tgg tat aat caa    768
Ala Leu Ser Pro Glu Ala Leu Thr Arg Leu Thr Thr Trp Tyr Asn Gln
                245                 250                 255 gct aaa gat ctg ctt aaa gat gat caa gta aag gac aaa tac gta gat    816
Ala Lys Asp Leu Leu Lys Asp Asp Gln Val Lys Asp Lys Tyr Val Asp
            260                 265                 270 ata ctt tca gtt caa aaa gct gtt gac caa gct tat gat cat gtg gaa    864
Ile Leu Ser Val Gln Lys Ala Val Asp Gln Ala Tyr Asp His Val Glu
        275                 280                 285 gag gga aaa ttt att acc act gat caa gca aat caa tta gct aac aag    912
Glu Gly Lys Phe Ile Thr Thr Asp Gln Ala Asn Gln Leu Ala Asn Lys
    290                 295                 300 cta cgt gat gct tta caa agt tta gaa tta aaa gat aaa aaa gta gcc    960
Leu Arg Asp Ala Leu Gln Ser Leu Glu Leu Lys Asp Lys Lys Val Ala
305                 310                 315                 320 aaa cca gta gct aaa ggt aca tac gat gtt aag tat gta gac aca gaa    1008
Lys Pro Val Ala Lys Gly Thr Tyr Asp Val Lys Tyr Val Asp Thr Glu
                325                 330                 335 gga aaa gaa gta gct aag tca cgt cac ttc gaa gga gaa gaa ggc gca    1056
Gly Lys Glu Val Ala Lys Ser Arg His Phe Glu Gly Glu Glu Gly Ala
            340                 345                 350 gct ttt gtc act tca gcg aaa gaa gta gcg ggt tac aaa ctt gtt aga    1104
Ala Phe Val Thr Ser Ala Lys Glu Val Ala Gly Tyr Lys Leu Val Arg
        355                 360                 365 acg gaa ggt gct gtt tca aat gtc ttc aca gca gga gca caa gta cgt    1152
Thr Glu Gly Ala Val Ser Asn Val Phe Thr Ala Gly Ala Gln Val Arg
    370                 375                 380 aca tat gtt tac gaa aaa gtt aaa cca gaa gtt aaa cca gac gtt aag    1200
Thr Tyr Val Tyr Glu Lys Val Lys Pro Glu Val Lys Pro Asp Val Lys
385                 390                 395                 400 cca gag gcc aaa cca gag gct aag cca gaa gtt aaa cca gac gtt aag    1248
Pro Glu Ala Lys Pro Glu Ala Lys Pro Glu Val Lys Pro Asp Val Lys
                405                 410                 415 cca gag gcc aaa cca gag gct aag cca gaa gtt aaa tca gac gtt aag    1296
Pro Glu Ala Lys Pro Glu Ala Lys Pro Glu Val Lys Ser Asp Val Lys
            420                 425                 430 cca gag gct aag cca gaa gcc aaa cca gag gct aaa cca gaa gtt aaa    1344
Pro Glu Ala Lys Pro Glu Ala Lys Pro Glu Ala Lys Pro Glu Val Lys
        435                 440                 445 cca gac gtt aag cca gag gct aaa cca gaa gcc aag cca gca acc aaa    1392
Pro Asp Val Lys Pro Glu Ala Lys Pro Glu Ala Lys Pro Ala Thr Lys
```

```
                450                 455                 460
aaa tcg gtt aat act agc gga aac ttg gtg gct aaa aaa gct att gaa   1440
Lys Ser Val Asn Thr Ser Gly Asn Leu Val Ala Lys Lys Ala Ile Glu
465                 470                 475                 480 aac aaa aag tat agt aaa aaa tta cca tca acg ggt gaa gcc gca agt   1488
Asn Lys Lys Tyr Ser Lys Lys Leu Pro Ser Thr Gly Glu Ala Ala Ser
                485                 490                 495 cca ctc tta gca att gta tca cta att gtt atg tta agt gca ggt ctt   1536
Pro Leu Leu Ala Ile Val Ser Leu Ile Val Met Leu Ser Ala Gly Leu
            500                 505                 510 att acg ata gtt tta aag cat aaa aaa aat taa                        1569
Ile Thr Ile Val Leu Lys His Lys Lys Asn
            515                 520

<210> SEQ ID NO 2
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asn Asn Asn Glu Lys Lys Val Lys Tyr Phe Leu Arg Lys Thr Ala
  1               5                  10                  15

Tyr Gly Leu Ala Ser Met Ser Ala Ala Phe Ile Val Cys Ser Gly Ile
                 20                  25                  30

Val Asn Thr Pro Thr Val Ser Ala Asp Ser Pro Asp Thr Leu Lys Val
             35                  40                  45

Glu Lys Leu Gly Lys Leu Lys Asp Val Lys Ser Val His Glu Leu Thr
         50                  55                  60

Pro Ile Ser Ile Pro Asn Glu Leu Lys Gly Ala Lys Glu Gln Ala Leu
 65                  70                  75                  80

Ser Ser Ile Ile Ser His Pro Asn Ile Thr Asn Ser Glu Val Asp Lys
                 85                  90                  95

Leu Ala Ser Asp Tyr Ser Phe Arg Ile Asn Thr Ser Asn Asp Val Asn
            100                 105                 110

Asp Val Lys Arg Leu Leu Asn Glu Phe Tyr Asn Ala Val Ala Arg Lys
        115                 120                 125

Gln Leu Asp Thr Asn Ser Ala Asp Tyr Arg Ser Lys Ile Asp Asn Ile
    130                 135                 140

Ser Thr Thr Gly Leu Ala Ile Ala Leu Glu Ala Lys Glu Ile Tyr Glu
145                 150                 155                 160

Ala Asn Lys Ser Ile Leu Pro His Arg Tyr Lys Asp Ser Val Gly Thr
                165                 170                 175

Tyr Val Asn Ser Phe Glu Glu Arg Arg Ser Pro Gly Lys Phe Asn Ile
            180                 185                 190

Trp Asn Gly Gln Glu Gly Phe Asn Ala Ala Gln Lys Leu Leu Glu Asp
        195                 200                 205

Val Lys Lys Leu Leu Leu Glu Leu Gln Asn Leu Thr Lys Asn Asn Lys
    210                 215                 220

Pro Asn Ile Gln Val Pro Lys Gln Ala Pro Thr Glu Ala Ala Lys Pro
225                 230                 235                 240

Ala Leu Ser Pro Glu Ala Leu Thr Arg Leu Thr Thr Trp Tyr Asn Gln
                245                 250                 255

Ala Lys Asp Leu Leu Lys Asp Asp Gln Val Lys Asp Lys Tyr Val Asp
            260                 265                 270
```

```
Ile Leu Ser Val Gln Lys Ala Val Asp Gln Ala Tyr Asp His Val Glu
        275                 280                 285

Glu Gly Lys Phe Ile Thr Thr Asp Gln Ala Asn Gln Leu Ala Asn Lys
    290                 295                 300

Leu Arg Asp Ala Leu Gln Ser Leu Glu Leu Lys Asp Lys Lys Val Ala
305                 310                 315                 320

Lys Pro Val Ala Lys Gly Thr Tyr Asp Val Lys Tyr Val Asp Thr Glu
                325                 330                 335

Gly Lys Glu Val Ala Lys Ser Arg His Phe Glu Gly Glu Glu Gly Ala
            340                 345                 350

Ala Phe Val Thr Ser Ala Lys Glu Val Ala Gly Tyr Lys Leu Val Arg
        355                 360                 365

Thr Glu Gly Ala Val Ser Asn Val Phe Thr Ala Gly Ala Gln Val Arg
    370                 375                 380

Thr Tyr Val Tyr Glu Lys Val Lys Pro Glu Val Lys Pro Asp Val Lys
385                 390                 395                 400

Pro Glu Ala Lys Pro Glu Ala Lys Pro Glu Val Lys Pro Asp Val Lys
                405                 410                 415

Pro Glu Ala Lys Pro Glu Ala Lys Pro Glu Val Lys Ser Asp Val Lys
            420                 425                 430

Pro Glu Ala Lys Pro Glu Ala Lys Pro Glu Ala Lys Pro Glu Val Lys
        435                 440                 445

Pro Asp Val Lys Pro Glu Ala Lys Pro Glu Ala Lys Pro Ala Thr Lys
    450                 455                 460

Lys Ser Val Asn Thr Ser Gly Asn Leu Val Ala Lys Lys Ala Ile Glu
465                 470                 475                 480

Asn Lys Lys Tyr Ser Lys Lys Leu Pro Ser Thr Gly Glu Ala Ala Ser
                485                 490                 495

Pro Leu Leu Ala Ile Val Ser Leu Ile Val Met Leu Ser Ala Gly Leu
            500                 505                 510

Ile Thr Ile Val Leu Lys His Lys Lys Asn
        515                 520

<210> SEQ ID NO 3
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(99)

<400> SEQUENCE: 3 atg aat aat aac gaa aaa aaa gta aaa tac ttt tta aga aaa aca gct     48
Met Asn Asn Asn Glu Lys Lys Val Lys Tyr Phe Leu Arg Lys Thr Ala
  1               5                  10                  15 tat ggt ttg gct tca atg tca gcg gcg ttt ata gta tgt agt ggt att     96
Tyr Gly Leu Ala Ser Met Ser Ala Ala Phe Ile Val Cys Ser Gly Ile
             20                  25                  30 gta                                                                  99
Val

<210> SEQ ID NO 4
<211> LENGTH: 33
<212> TYPE: PRT
<213> ORGANISM: Artificial Sequence
```

<220> FEATURE:
<223> OTHER INFORMATION: Description of Artificial Sequence: Synthetic
    peptide

<400> SEQUENCE: 4

Met Asn Asn Asn Glu Lys Lys Val Lys Tyr Phe Leu Arg Lys Thr Ala
1               5                   10                  15

Tyr Gly Leu Ala Ser Met Ser Ala Ala Phe Ile Val Cys Ser Gly Ile
            20                  25                  30

Val

<210> SEQ ID NO 5
<211> LENGTH: 570
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: CDS
<222> LOCATION: (1)..(570)

<400> SEQUENCE: 5 aat act cct aca gtg tct gct gat agt cct gat aca tta aaa gtc gaa      48
Asn Thr Pro Thr Val Ser Ala Asp Ser Pro Asp Thr Leu Lys Val Glu
1               5                   10                  15 aaa tta ggc aaa ttg aaa gat gtg aaa tca gtt cat gaa ctc aca ccc      96
Lys Leu Gly Lys Leu Lys Asp Val Lys Ser Val His Glu Leu Thr Pro
            20                  25                  30 ata tca ata ccg aac gaa tta aaa ggt gct aaa gag caa gca ctt tct      144
Ile Ser Ile Pro Asn Glu Leu Lys Gly Ala Lys Glu Gln Ala Leu Ser
        35                  40                  45 tca ata att tca cat cct aat ata act aat tcg gaa gta gac aaa cta      192
Ser Ile Ile Ser His Pro Asn Ile Thr Asn Ser Glu Val Asp Lys Leu
    50                  55                  60 gct agt gac tat agt ttt aga att aat aca tct aat gat gtg aac gac      240
Ala Ser Asp Tyr Ser Phe Arg Ile Asn Thr Ser Asn Asp Val Asn Asp
65                  70                  75                  80 gtt aaa cgt cta tta aat gaa ttt tat aac gca gtt gca agg aaa cag      288
Val Lys Arg Leu Leu Asn Glu Phe Tyr Asn Ala Val Ala Arg Lys Gln
                85                  90                  95 tta gat aca aat tct gct gac tac cgt agt aaa att gat aat atc agt      336
Leu Asp Thr Asn Ser Ala Asp Tyr Arg Ser Lys Ile Asp Asn Ile Ser
            100                 105                 110 act aca ggt ctt gcg ata gct ctt gag gct aaa gaa att tat gaa gca      384
Thr Thr Gly Leu Ala Ile Ala Leu Glu Ala Lys Glu Ile Tyr Glu Ala
        115                 120                 125 aat aaa tct ata tta cct cat cgt tac aaa gat tct gtt gga act tat      432
Asn Lys Ser Ile Leu Pro His Arg Tyr Lys Asp Ser Val Gly Thr Tyr
    130                 135                 140 gtg aac agt ttt gag gaa aga cga agt cca gga aaa ttt aat att tgg      480
Val Asn Ser Phe Glu Glu Arg Arg Ser Pro Gly Lys Phe Asn Ile Trp
145                 150                 155                 160 aat ggt cag gaa gga ttt aat gca gct caa aaa ttg tta gaa gat gtt      528
Asn Gly Gln Glu Gly Phe Asn Ala Ala Gln Lys Leu Leu Glu Asp Val
                165                 170                 175 aaa aaa tta tta ctt gag cta caa aat tta aca aaa aat aac              570
Lys Lys Leu Leu Leu Glu Leu Gln Asn Leu Thr Lys Asn Asn
            180                 185                 190

<210> SEQ ID NO 6
<211> LENGTH: 190

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asn Thr Pro Thr Val Ser Ala Asp Ser Pro Asp Thr Leu Lys Val Glu
 1               5                  10                  15

Lys Leu Gly Lys Leu Lys Asp Val Lys Ser Val His Glu Leu Thr Pro
             20                  25                  30

Ile Ser Ile Pro Asn Glu Leu Lys Gly Ala Lys Glu Gln Ala Leu Ser
         35                  40                  45

Ser Ile Ile Ser His Pro Asn Ile Thr Asn Ser Glu Val Asp Lys Leu
     50                  55                  60

Ala Ser Asp Tyr Ser Phe Arg Ile Asn Thr Ser Asn Asp Val Asn Asp
 65                  70                  75                  80

Val Lys Arg Leu Leu Asn Glu Phe Tyr Asn Ala Val Ala Arg Lys Gln
                 85                  90                  95

Leu Asp Thr Asn Ser Ala Asp Tyr Arg Ser Lys Ile Asp Asn Ile Ser
            100                 105                 110

Thr Thr Gly Leu Ala Ile Ala Leu Glu Ala Lys Glu Ile Tyr Glu Ala
        115                 120                 125

Asn Lys Ser Ile Leu Pro His Arg Tyr Lys Asp Ser Val Gly Thr Tyr
130                 135                 140

Val Asn Ser Phe Glu Glu Arg Arg Ser Pro Gly Lys Phe Asn Ile Trp
145                 150                 155                 160

Asn Gly Gln Glu Gly Phe Asn Ala Ala Gln Lys Leu Leu Glu Asp Val
                165                 170                 175

Lys Lys Leu Leu Leu Glu Leu Gln Asn Leu Thr Lys Asn Asn
            180                 185                 190

<210> SEQ ID NO 7
<211> LENGTH: 291
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(291)

<400> SEQUENCE: 7 aaa cca aat att caa gta cct aaa caa gca cct aca gaa gct gca aaa    48
Lys Pro Asn Ile Gln Val Pro Lys Gln Ala Pro Thr Glu Ala Ala Lys
 1               5                  10                  15 cca gct ttg tca cca gaa gcc ttg aca aga ttg act aca tgg tat aat    96
Pro Ala Leu Ser Pro Glu Ala Leu Thr Arg Leu Thr Thr Trp Tyr Asn
             20                  25                  30 caa gct aaa gat ctg ctt aaa gat gat caa gta aag gac aaa tac gta   144
Gln Ala Lys Asp Leu Leu Lys Asp Asp Gln Val Lys Asp Lys Tyr Val
         35                  40                  45 gat ata ctt tca gtt caa aaa gct gtt gac caa gct tat gat cat gtg   192
Asp Ile Leu Ser Val Gln Lys Ala Val Asp Gln Ala Tyr Asp His Val
     50                  55                  60 gaa gag gga aaa ttt att acc act gat caa gca aat caa tta gct aac   240
Glu Glu Gly Lys Phe Ile Thr Thr Asp Gln Ala Asn Gln Leu Ala Asn
 65                  70                  75                  80 aag cta cgt gat gct tta caa agt tta gaa tta aaa gat aaa aaa gta   288

```
Lys Leu Arg Asp Ala Leu Gln Ser Leu Glu Leu Lys Asp Lys Lys Val
             85                  90                  95 gcc                                                                  291
Ala

<210> SEQ ID NO 8
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Lys Pro Asn Ile Gln Val Pro Lys Gln Ala Pro Thr Glu Ala Ala Lys
  1               5                  10                  15

Pro Ala Leu Ser Pro Glu Ala Leu Thr Arg Leu Thr Thr Trp Tyr Asn
             20                  25                  30

Gln Ala Lys Asp Leu Leu Lys Asp Asp Gln Val Lys Asp Lys Tyr Val
         35                  40                  45

Asp Ile Leu Ser Val Gln Lys Ala Val Asp Gln Ala Tyr Asp His Val
     50                  55                  60

Glu Glu Gly Lys Phe Ile Thr Thr Asp Gln Ala Asn Gln Leu Ala Asn
 65                  70                  75                  80

Lys Leu Arg Asp Ala Leu Gln Ser Leu Glu Leu Lys Asp Lys Lys Val
             85                  90                  95

Ala

<210> SEQ ID NO 9
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(180)

<400> SEQUENCE: 9 aag cca gag gcc aaa cca gag gct aag cca gaa gtt aaa cca gac gtt     48
Lys Pro Glu Ala Lys Pro Glu Ala Lys Pro Glu Val Lys Pro Asp Val
  1               5                  10                  15 aag cca gag gcc aaa cca gag gct aag cca gaa gtt aaa tca gac gtt     96
Lys Pro Glu Ala Lys Pro Glu Ala Lys Pro Glu Val Lys Ser Asp Val
             20                  25                  30 aag cca gag gct aag cca gaa gcc aaa cca gag gct aaa cca gaa gtt    144
Lys Pro Glu Ala Lys Pro Glu Ala Lys Pro Glu Ala Lys Pro Glu Val
         35                  40                  45 aaa cca gac gtt aag cca gag gct aaa cca gaa gcc                    180
Lys Pro Asp Val Lys Pro Glu Ala Lys Pro Glu Ala
     50                  55                  60

<210> SEQ ID NO 10
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Lys Pro Glu Ala Lys Pro Glu Ala Lys Pro Glu Val Lys Pro Asp Val
```

```
                1               5                      10                     15
Lys Pro Glu Ala Lys Pro Glu Ala Lys Pro Glu Val Lys Ser Asp Val
                        20                     25                     30

Lys Pro Glu Ala Lys Pro Glu Ala Lys Pro Glu Ala Lys Pro Glu Val
                35                     40                     45

Lys Pro Asp Val Lys Pro Glu Ala Lys Pro Glu Ala
    50                     55                     60

<210> SEQ ID NO 11
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(189)

<400> SEQUENCE: 11 aag cca gca acc aaa aaa tcg gtt aat act agc gga aac ttg gtg gct        48
Lys Pro Ala Thr Lys Lys Ser Val Asn Thr Ser Gly Asn Leu Val Ala
  1               5                   10                  15 aaa aaa gct att gaa aac aaa aag tat agt aaa aaa tta cca tca acg        96
Lys Lys Ala Ile Glu Asn Lys Lys Tyr Ser Lys Lys Leu Pro Ser Thr
             20                  25                  30 ggt gaa gcc gca agt cca ctc tta gca att gta tca cta att gtt atg      144
Gly Glu Ala Ala Ser Pro Leu Leu Ala Ile Val Ser Leu Ile Val Met
         35                  40                  45 tta agt gca ggt ctt att acg ata gtt tta aag cat aaa aaa aat taa      192
Leu Ser Ala Gly Leu Ile Thr Ile Val Leu Lys His Lys Lys Asn
     50                  55                  60

<210> SEQ ID NO 12
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Lys Pro Ala Thr Lys Lys Ser Val Asn Thr Ser Gly Asn Leu Val Ala
  1               5                   10                  15

Lys Lys Ala Ile Glu Asn Lys Lys Tyr Ser Lys Lys Leu Pro Ser Thr
             20                  25                  30

Gly Glu Ala Ala Ser Pro Leu Leu Ala Ile Val Ser Leu Ile Val Met
         35                  40                  45

Leu Ser Ala Gly Leu Ile Thr Ile Val Leu Lys His Lys Lys Asn
     50                  55                  60

<210> SEQ ID NO 13
<211> LENGTH: 216
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(216)

<400> SEQUENCE: 13 aaa cca gta gct aaa ggt aca tac gat gtt aag tat gta gac aca gaa        48
```

```
Lys Pro Val Ala Lys Gly Thr Tyr Asp Val Lys Tyr Val Asp Thr Glu
 1               5                  10                  15 gga aaa gaa gta gct aag tca cgt cac ttc gaa gga gaa gaa ggc gca      96
Gly Lys Glu Val Ala Lys Ser Arg His Phe Glu Gly Glu Glu Gly Ala
             20                  25                  30 gct ttt gtc act tca gcg aaa gaa gta gcg ggt tac aaa ctt gtt aga     144
Ala Phe Val Thr Ser Ala Lys Glu Val Ala Gly Tyr Lys Leu Val Arg
         35                  40                  45 acg gaa ggc gct gtt tca aat gtc ttc aca gca gga gca caa gta cgt     192
Thr Glu Gly Ala Val Ser Asn Val Phe Thr Ala Gly Ala Gln Val Arg
     50                  55                  60 aca tat gtt tac gaa aaa gta gcc                                     216
Thr Tyr Val Tyr Glu Lys Val Ala
 65                  70
```

<210> SEQ ID NO 14
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Lys Pro Val Ala Lys Gly Thr Tyr Asp Val Lys Tyr Val Asp Thr Glu
 1               5                  10                  15

Gly Lys Glu Val Ala Lys Ser Arg His Phe Glu Gly Glu Glu Gly Ala
             20                  25                  30

Ala Phe Val Thr Ser Ala Lys Glu Val Ala Gly Tyr Lys Leu Val Arg
         35                  40                  45

Thr Glu Gly Ala Val Ser Asn Val Phe Thr Ala Gly Ala Gln Val Arg
     50                  55                  60

Thr Tyr Val Tyr Glu Lys Val Ala
 65                  70
```

<210> SEQ ID NO 15
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(237)

<400> SEQUENCE: 15

```
aaa cca gta gct aaa ggt aca tac gat gtt aag tat gta gac aca gaa      48
Lys Pro Val Ala Lys Gly Thr Tyr Asp Val Lys Tyr Val Asp Thr Glu
 1               5                  10                  15 gga aaa gaa gta gct aag tca cgt cac ttc gaa gga gaa gaa ggc gca      96
Gly Lys Glu Val Ala Lys Ser Arg His Phe Glu Gly Glu Glu Gly Ala
             20                  25                  30 gct ttt gtc act tca gcg aaa gaa gta gcg ggt tac aaa ctt gtt aga     144
Ala Phe Val Thr Ser Ala Lys Glu Val Ala Gly Tyr Lys Leu Val Arg
         35                  40                  45 acg gaa ggt gct gtt tca aat gtc ttc aca gca gga gca caa gta cgt     192
Thr Glu Gly Ala Val Ser Asn Val Phe Thr Ala Gly Ala Gln Val Arg
     50                  55                  60 aca tat gtt tac gaa aaa gtt aaa cca gaa gtt aaa cca gac gtt         237
Thr Tyr Val Tyr Glu Lys Val Lys Pro Glu Val Lys Pro Asp Val
 65                  70                  75
```

<210> SEQ ID NO 16
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Lys Pro Val Ala Lys Gly Thr Tyr Asp Val Lys Tyr Val Asp Thr Glu
 1               5                  10                  15

Gly Lys Glu Val Ala Lys Ser Arg His Phe Glu Gly Glu Glu Gly Ala
            20                  25                  30

Ala Phe Val Thr Ser Ala Lys Glu Val Ala Gly Tyr Lys Leu Val Arg
        35                  40                  45

Thr Glu Gly Ala Val Ser Asn Val Phe Thr Ala Gly Ala Gln Val Arg
    50                  55                  60

Thr Tyr Val Tyr Glu Lys Val Lys Pro Glu Val Lys Pro Asp Val
65                  70                  75

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaaataaacg tggtcctatc ct                                          22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggcaaagttc tgatgaggtt tg                                          22

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcagcgtttg ctgtatgtag tggt                                        24

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cttgagaacg tcttgactgc                                             20

-continued

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ggtaagcagt caagacgttc tca                                        23

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
agttcccaca gagtctgcat                                            20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
agcacaggaa gttgcccaga aa                                         22

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
agcatcacgt agcttgttag                                            20

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gttgaccaag cttatgatca tgtgg                                      25

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
ttgctaagag tggacttgcg                                            20

<210> SEQ ID NO 27

```
<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggcttcaatg tcagcggcgt ttat                                          24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gctgcattaa atccttcctg acca                                          24

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cctcatcgtt acaaagattc tg                                            22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agccaccaag tttccgctag ta                                            22

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttgacaggtc tctatgattt agtc                                          24

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtctggttct cagcctaatt c                                             21

<210> SEQ ID NO 33
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atacaaattc tgctgactac cg                                              22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttaaatcctt cctgaccatt cc                                              22

<210> SEQ ID NO 35
<211> LENGTH: 208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atacaaattc tgctgactac cgtagtaaaa ttgataatat cagtactaca ggtcttgcga      60
tagctcttga ggctaaagaa atttatgaag caaataaatc tatattacct catcgttaca    120
aagattctgt tggaacttat gtgaacagtt ttgaggaaag acgaagtcca ggaaaattta    180
atatttggaa tggtcaggaa ggatttaa                                      208

<210> SEQ ID NO 36
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
cctcatcgtt acaaagattc tgttggaact tatgtgaaca gttttgagga aagacgaagt     60
ccaggaaaat ttaatatttg gaatggtcag gaaggattta a                       101

<210> SEQ ID NO 37
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
cctcatcgtt acaaagattc tgttggaact tatgtgaaca gttttgagga aagacgaagt     60
ccaggaaaat ttaatatttg gaatggtcag gaaggattta atgcagc                 107

<210> SEQ ID NO 38
<211> LENGTH: 214
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 38

```
atacaaattc tgctgactac cgtagtaaaa ttgataatat cagtactaca ggtcttgcga      60
tagctcttga ggctaaagaa atttatgaag caaataaatc tatattacct catcgttaca     120
aagattctgt tggaacttat gtgaacagtt ttgaggaaag acgaagtcca ggaaaattta     180
atatttggaa tggtcaggaa ggatttaatg cagc                                 214
```

<210> SEQ ID NO 39
<211> LENGTH: 543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
ggcttcaatg tcagcggcgt ttatagtatg tagtggtatt gtaaatactc ctacagtgtc      60
tgctgatagt cctgatacat taaaagtcga aaaattaggc aaattgaaag atgtgaaatc     120
agttcatgaa ctcacaccca tatcaatacc gaacgaatta aaaggtgcta agagcaagc     180
actttcttca ataatttcac atcctaatat aactaattcg gaagtagaca aactagctag     240
tgactatagt tttagaatta atacatctaa tgatgtgaac gacgttaaac gtctattaaa     300
tgaattttat aacgcagttg caaggaaaca gttagataca aattctgctg actaccgtag     360
taaaattgat aatatcagta ctacaggtct tgcgatagct cttgaggcta agaaattta     420
tgaagcaaat aaatctatat tacctcatcg ttacaaagat tctgttggaa cttatgtgaa     480
cagttttgag gaaagacgaa gtccaggaaa atttaatatt tggaatggtc aggaaggatt     540
taa                                                                  543
```

<210> SEQ ID NO 40
<211> LENGTH: 549
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
ggcttcaatg tcagcggcgt ttatagtatg tagtggtatt gtaaatactc ctacagtgtc      60
tgctgatagt cctgatacat taaaagtcga aaaattaggc aaattgaaag atgtgaaatc     120
agttcatgaa ctcacaccca tatcaatacc gaacgaatta aaaggtgcta agagcaagc     180
actttcttca ataatttcac atcctaatat aactaattcg gaagtagaca aactagctag     240
tgactatagt tttagaatta atacatctaa tgatgtgaac gacgttaaac gtctattaaa     300
tgaattttat aacgcagttg caaggaaaca gttagataca aattctgctg actaccgtag     360
taaaattgat aatatcagta ctacaggtct tgcgatagct cttgaggcta agaaattta     420
tgaagcaaat aaatctatat tacctcatcg ttacaaagat tctgttggaa cttatgtgaa     480
cagttttgag gaaagacgaa gtccaggaaa atttaatatt tggaatggtc aggaaggatt     540
taatgcagc                                                            549
```

<210> SEQ ID NO 41
<211> LENGTH: 20
<212> TYPE: DNA
<213> ORGANISM: Artificial Sequence -continued
<220> FEATURE:
<223> OTHER INFORMATION: Description of Artificial Sequence: Synthetic
      primer

<400> SEQUENCE: 41
gaataacact tattcctatc                                                   20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cttccacagt agttcaccac c                                                 21

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Any amino acid

<400> SEQUENCE: 43

Leu Pro Xaa Thr Gly
 1               5

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Pro Glu Ala
 1

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Thr or Lys

<400> SEQUENCE: 45

Ile Lys Ala Glu Ser Ile Asn Xaa
 1               5

<210> SEQ ID NO 46
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 46

Lys Pro Glu Ala Lys Pro Glu Ala Lys Pro Glu Ala Lys Pro Glu Ala
 1               5                  10                  15

Lys Pro Glu Ala Lys Pro Glu Ala Lys Pro Glu Ala Lys Pro Glu Ala
            20                  25                  30

Lys Pro Glu Ala Lys Pro Glu Ala Lys Pro Glu Ala Lys Pro Glu Ala
        35                  40                  45

Lys Pro Glu Ala Lys Pro Glu Ala Lys Pro Glu Ala Lys Pro Glu Ala
    50                  55                  60

Lys Pro Glu Ala Lys Pro Glu Ala
 65                  70

<210> SEQ ID NO 47
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Lys Pro Glu Ala Lys Pro Glu Ala Lys Pro Glu Ala Lys Pro Glu Ala
 1               5                  10                  15

Lys Pro Glu Ala Lys Pro Glu Ala Lys Pro Glu Ala Lys Pro Glu Ala
            20                  25                  30

Lys Pro Glu Ala Lys Pro Glu Ala Lys Pro Glu Ala Lys Pro Glu Ala
        35                  40                  45

Lys Pro Glu Ala Lys Pro Glu Ala Lys Pro Glu Ala Lys Pro Glu Ala
    50                  55                  60

Lys Pro Glu Ala Lys Pro Glu Ala Lys Pro Glu Ala Lys Pro Glu Ala
 65                  70                  75                  80

Lys Pro Glu Ala Lys Pro Glu Ala
                85

<210> SEQ ID NO 48
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Lys Pro Glu Ala Lys Pro Glu Ala Lys Pro Glu Ala Lys Pro Glu Ala
 1               5                  10                  15

Lys Pro Glu Ala Lys Pro Glu Ala Lys Pro Glu Ala Lys Pro Glu Ala
            20                  25                  30

Lys Pro Glu Ala Lys Pro Glu Ala Lys Pro Glu Ala Lys Pro Glu Ala
        35                  40                  45

Lys Pro Glu Ala Lys Pro Glu Ala Lys Pro Glu Ala
    50                  55                  60
```